US006342352B1

(12) United States Patent
Schuch et al.

(10) Patent No.: US 6,342,352 B1
(45) Date of Patent: Jan. 29, 2002

(54) METHOD OF DETECTING SHIGELLA AND SHIGELLA MXIM DNA

(75) Inventors: Raymond Schuch, Washington, DC (US); Robin C. Sandlin, Columbia; Anthony T. Maurelli, Silver Spring, both of MD (US)

(73) Assignee: The Henry M. Jackson Foundation for the Advancement of Military Medicine, Rockville, MD (US)

( * ) Notice: Subject to any disclaimer, the term of this patent is extended or adjusted under 35 U.S.C. 154(b) by 0 days.

(21) Appl. No.: 09/296,670

(22) Filed: Apr. 22, 1999

Related U.S. Application Data
(60) Provisional application No. 60/082,944, filed on Apr. 24, 1998.

(51) Int. Cl.[7] .......................... C12Q 1/68; G01N 33/53; G01N 33/554; G01N 33/532
(52) U.S. Cl. .......................... 435/6; 435/7.2; 435/7.32; 436/544
(58) Field of Search ........................... 435/6, 7.2, 7.32; 436/544; 935/77, 78, 76; 536/23.1

(56) References Cited

FOREIGN PATENT DOCUMENTS

| WO | WO 86/00646 | 1/1986 |
| WO | WO 97/40063 | 10/1997 |

OTHER PUBLICATIONS

Schuch, Raymond; Sandlin, Robin C.; and Maurelli, Anthony T., "A system for identifying post–invasion functions of invasion genes:requirements for the Mxi–Spa type III secretion pathway of *Shigella flexneri* in intercellular dissemination,"*Molecular Microbiology*, vol. 34, No. 4, pp. 675–689 (1999).
International Search Report, dated Nov. 17, 1999.
Lampel, Keith A.;Jagow, James A.; Trucksess, Mary; and Hill, Walter E., "Polymerase Chain Reaction for Detection of Invasive *Shigella flexneri* in Food," *Applied and Environmental Microbiology*, vol. 56 No. 6, Jun. 1990, pp. 1536–1540.
Mason, Hugh S. and Arntzen, Charles J., "Transgenic plants as vaccine production systems," *Trends in Biotechnology*vol. 13, Sep., 1995, pp. 388–887.
Panyutin, Igor G. and Neumann, Ronald D., "Radioprobing of DNA: distribution of DNA breaks produced by decay of $^{125}$I incorporated into a triplex–forming oligonucleotide correlates with geometry of the triplex," *Nucleic Acids Research*, vol. 25, No. 4, 1997, pp. 883–887.

Schuch, Raymond and Maurelli, Anthony T., "The Mxi–Spa Type III Secretory Pathway of *Shigella flexneri* Requires an Outer Membrane Lipoprotein, MxiM, for Invasin Translocation," *Infection and Immunity*, vol. 67, No. 4, Apr. 1999, pp. 1982–1991.
Allaoui, A., Sansonetti, P.J., and Parsot, C. (1992), "MxiJ, a lipoprotein involved in secretion of Shigella Ipa invasins, is homologous to YscJ, a secretion factor of the Yersinia Yop protein," *J. Bacteriol.* 174:7991–7669.
Guzman, L. –M., Belin, D., Carson, M.J., and Beckwith, J. (1995), "Tight regulation, modulation, and high–level expression by vectors containing the arabinose $P_{BAD}$ promoter," *J. Bacteriol.* 177:4121–4130.
Hsia, R., Small, P.L.C., and Bavoil, P. M. (1993), "Characterizations of virulence Genes of Enteroinvasive *Escherichia coli* by TnogiA Mutagenesis; Identification of invX, a Gene Required for Entry into Hep–2 Cells," *J. Bacteriol.*, 175:4817–4823.
Schuch, R., and Maurelli, A.T. (1999), "The Mxi–Spa type III secretary pathway of *Shigella flexneri* requires an outer membrane lipoprotein, MxiM, for invasin translocation," *Infect. Immun.* 67:1982–1991.
Sizemore, D.R, Branstrom, A.A., and Sadoff, J.C. (1995), "Attenuated Shigella as a DNA delivery vehicle for DNA–mediated baimmunization," *Science* 270:299–302.
Sizemore, D.R., Branstrom, A.A., and Sadoff, J.C. (1997), "Attenuated bacteria as a DNA delivery vehicle for DNA–mediated immunization," *Vaccine* 15(8):804–807.

*Primary Examiner*—S. Devi
(74) *Attorney, Agent, or Firm*—Finnegan, Henderson, Farabow, Garrett & Dunner, L.L.P.

(57) ABSTRACT

The present invention relates to our discovery that the mxiM protein of *Shigella flexneri* is indispensable for the spread of Shigella from cell to cell. Thus, the invention provides the mxiM protein or peptides or portions thereof as antigens in vaccines to prevent Shigella infections and treat hosts infected with Shigella by inhibiting intercellular spread. In another aspect, the invention relates to antibodies generated against the mxiM proteins, peptides, or portions thereof to detect Shigella in contaminated food and water supplies as well as in infected hosts. The present invention also describes a method called the TIER (test of intracellular expression requirements) for determining the intracellular expression requirements of genes and therefore, permitting one to establish the role of genes in the pathogenesis of organisms. A method of detecting Shigella or Shigella mxiM DNA in a sample using a mxiM DNA probe is also described.

3 Claims, 8 Drawing Sheets

Figure 1A:
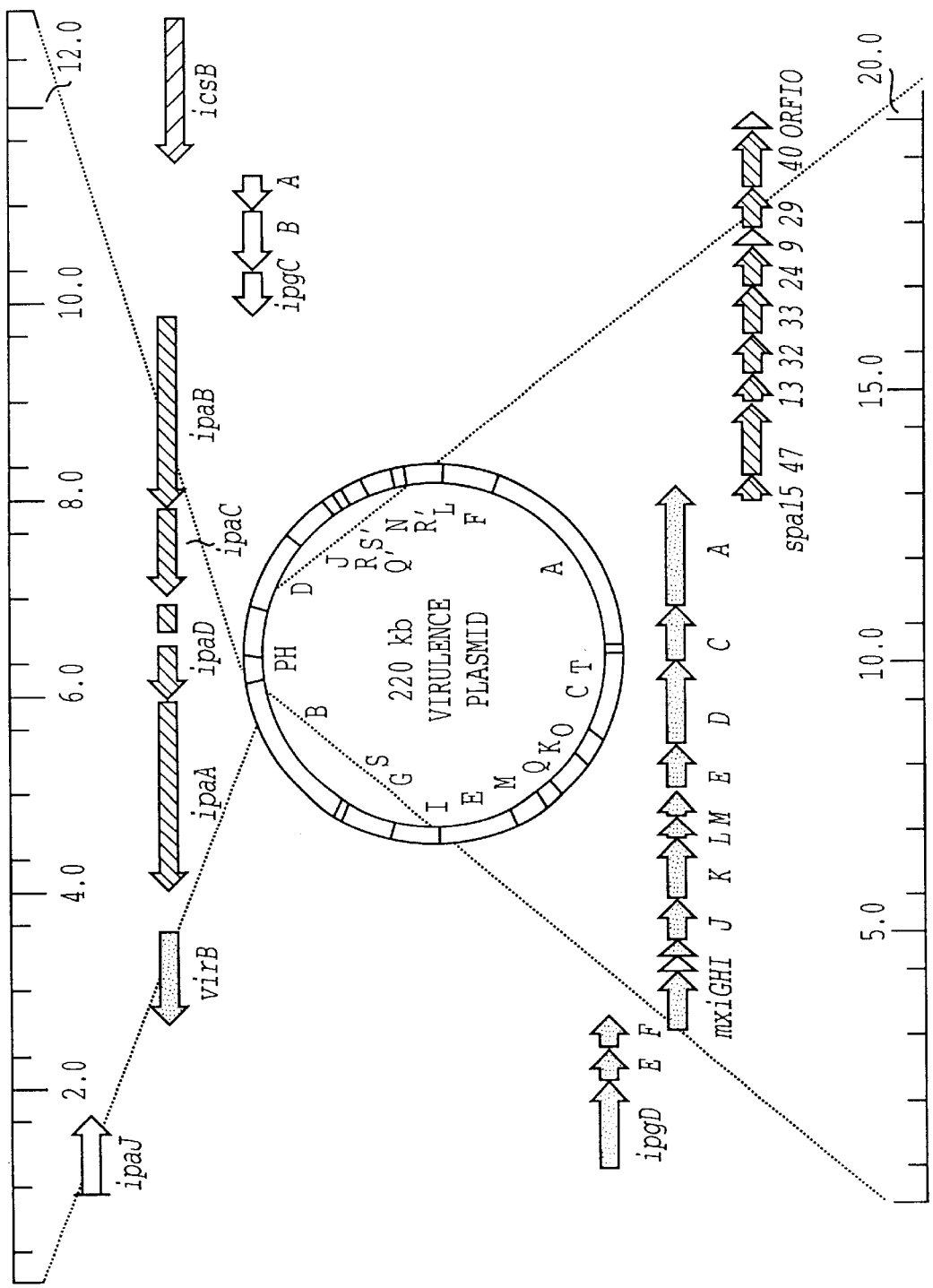

SEQUENCE LISTING

```
<160> NUMBER OF SEQ ID NOS: 2

<210> SEQ ID NO 1
<211> LENGTH: 600
<212> TYPE: DNA
<213> ORGANISM: Shigella flexneri
```

-continued

```
<400> SEQUENCE: 1
ttaattagtg tctttgaagc agggagagag gcagatgatt cgacatggta gtaataagtt      60
gaaatatttt attttaagta tattgctatt aacactgagt gggtgtgctt taaagtcatc     120
atctaattct gaaaaagaat ggcatattgt tcctgtaagt aaggattatt tttctattcc     180
aaatgattta ttatggtcgt ttaatacaac caataaaagt ataaatgttt actctaaatg     240
tattagtggt aaggcggttt atagttttaa tgcaggtaaa ttcatgggca actttaatgt     300
taaggaagta gatgggtgct tcatggatgc acaaaagata gctatagata aactattttc     360
tatgctgaaa gacggggttg ttttaaaagg taataagata aatgatacca tccttataga     420
gaaggatggg gaagttaaat taaaattaat tcgagggata taattgtatt gtgagtaaat     480
ataaaggtct aaatacaagt aatatgtttt acatttactc tagtggacat gaaccagtta     540
acgttgagct tgtaaaagat aaagaacgta acataattga gctggctcca gcatggaagg     600

<210> SEQ ID NO 2
<211> LENGTH: 142
<212> TYPE: PRT
<213> ORGANISM: Shigella flexneri

<400> SEQUENCE: 2

Met Ile Arg His Gly Ser Asn Lys Leu Lys Ile Phe Ile Leu Ser Ile
  1               5                  10                  15

Leu Leu Thr Leu Ser Gly Cys Ala Leu Lys Ser Ser Ser Asn Ser
             20                  25                  30

Glu Lys Glu Trp His Ile Val Pro Val Ser Lys Asp Tyr Phe Ser Ile
         35                  40                  45

Pro Asn Asp Leu Leu Trp Ser Phe Asn Thr Thr Asn Lys Ser Ile Asn
     50                  55                  60

Val Tyr Ser Lys Cys Ile Ser Gly Lys Ala Val Tyr Ser Phe Asn Ala
 65                  70                  75                  80

Gly Lys Phe Met Gly Asn Phe Asn Val Lys Glu Val Asp Gly Cys Phe
                 85                  90                  95

Met Asp Ala Gln Lys Ile Ala Ile Asp Lys Leu Phe Ser Met Leu Lys
            100                 105                 110

Asp Gly Val Val Leu Lys Gly Asn Lys Ile Asn Asp Thr Ile Leu Ile
        115                 120                 125

Glu Lys Asp Gly Glu Val Lys Leu Lys Leu Ile Arg Gly Ile
    130                 135                 140
```

METHOD OF DETECTING SHIGELLA AND SHIGELLA MXIM DNA

RELATED APPLICATIONS

This application is related to U.S. provisional patent application 60/082,944, filed Apr. 24, 1998, which is herein incorporated by reference.

GOVERNMENT INTEREST

The invention described herein may be manufactured, licensed, and used for governmental purposes without payment of royalties to us thereon.

FIELD OF THE INVENTION

The present invention relates to proteins that direct the secretion of virulence proteins of pathogenic bacteria such as Shigellae and the use of such proteins, peptides, and fragments thereof to detect, prevent and treat disease. The invention also relates to a method of determining the intracellular requirements of genes of pathogenic organisms that invade, colonize, persist and cause disease in the host.

BACKGROUND OF THE INVENTION

Bacteria of the genus Shigella are gram negative enteric pathogens which are the causative agents of bacillary dysentery or shigellosis. Shigella infection accounts for a considerable fraction of acute diarrheal diseases worldwide and is an important public health problem in developing countries where bacillary dysentery remains a major cause of childhood mortality. The worldwide incidence of bacillary dysentery is estimated to exceed 200 million cases annually. About 5 million cases require hospitalization and about 650,000 persons die of shigellosis each year (Institute of Medicine, 1986). Shigellosis continues to be an important public health concern even in the United States with over 32,000 cases reported in 1995 (Centers for Disease Control, 1995). Of principal importance are food borne outbreaks and outbreaks in institutional settings (day care centers, nursing homes, ect.) and on Indian reservations. The clinical presentation of shigellosis can range from a mild diarrhea to severe dysentery with frequent passage of bloody, mucoid, small volume stools. The disease is characterized by extensive damage to the colonic epithelial layer, cell death, ulceration and inflammation of the colon. While infections are usually self-limit and do not spread from the lamina propria to the submucosa, shigellosis can be life-threatening in young or malnourished patients (DuPont et al., 1995). There exists no effective vaccine against shigellosis.

The primary means of human to human transmission of Shigella is by the fecal-oral route. Most cases of shigellosis are caused by the ingestion of fecally-contaminated food or water. In the case of foods, the major factor for contamination is the poor personal hygiene of food handlers, particularly in view of the low infectious dose of Shigella spp. Volunteer studies showed that the $ID_{50}$ (the infectious dose required to cause disease in 50% of the volunteers) of Shigella is as low as 200 shigellae, although it has been reported that the ingestion of as few as 10 organisms is sufficient to cause disease (DuPont et al., 1989).

The low $ID_{50}$ of Shigella accounts for its high communicability, particularly in impoverished and crowded populations. One consequence of this feature is that a contaminated food source has the potential to cause explosive outbreaks of dysentery with secondary cases likely to occur among close contacts of infected individuals. Thus, infected food handlers can contaminate food and spread infection among large numbers of individuals. Several examples of food borne outbreaks of shigellosis are described in Maurelli et al., 1997. In particular, day care workers and children attending day care facilities are placed at risk when a child infected with Shigella is present. The bacteria are shed in feces and the immature personal hygiene habits of very young children can easily lead to infection of other children as well as care providers (Mohle-Boetani et al., 1995).

With a low infectious dose required to cause disease coupled with oral transmission via fecally-contaminated food and water, it is not surprising that dysentery caused by Shigella spp. follows in the wake of many natural (earthquakes, floods, famine) and man-made disasters (war). Civil wars in Burundi and Rwanda led to massive movement of refugees. An outbreak of dysentery in a refugee camp in Rwanda in late 1993 affected more than 6,000 people (attack rate >32%), mostly children under five years old (Paquet et al., 1995). In August, 1994, more than 15,500 cases of bloody diarrhea were reported from three refugee camps in Zaire (Centers for Disease Control, 1996).

When natural or man-made disasters destroy the sanitary waste treatment and water purification infrastructure, developed countries assume the conditions of developing countries. These conditions place a population at risk for diarrheal diseases such as cholera and dysentery. Recent examples include the war in Bosnia-Herzegovina, and famine and political upheaval in Somalia (Levine et al., 1994). All of these factors are exacerbated by the fact that Shigellae are becoming increasingly resistant to most antimicrobial agents commonly used in the treatment of diarrheal diseases (Centers for Disease Control, 1994).

There are four species of the genus Shigella serologically grouped (39 serotypes) based on their somatic O-antigens: Shigella dysenteriae (group A; 10 O groups), S. flexneri (group B; 13 O groups), S. boydii (group C; 15 O groups), and S. sonnei (group D; 1 O type). As members of the family Enterobacteriaceae, they are nearly genetically identical to Escherichia coli and closely related to Salmonella and Citrobacter (Ochman et al., 1983). One class of E. coli, the enteroinvasive E. coli (EIEC), has pathogenic properties that are similar to Shigella. EIEC cause a disease that is clinically similar to bacillary dysentery, and these bacteria harbor a large plasmid that has the same genetic determinants for virulence as Shigella. EIEC share certain biochemical properties with Shigella such as being nonmotile and unable to synthesize lysine decarboxylase. In addition, some serogroups of EIEC share identical O-antigens with certain Shigella serotypes (Sansonetti et al., 1985). However, despite these differences, strains of EIEC and Shigella express many of the same biochemical characteristics as E. coli. This biochemical similarity can pose problems in distinguishing these pathogens from E. coli found in normal flora.

Figure 5A:
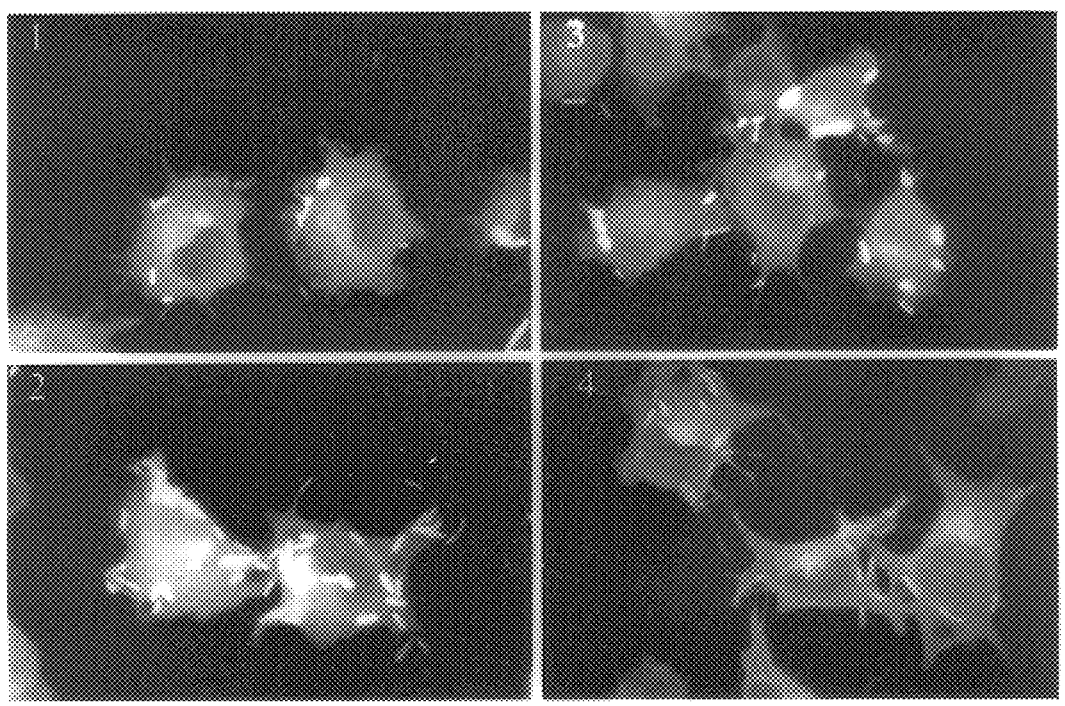

The clinical symptoms of shigellosis can be directly attributed to the hallmarks of Shigella virulence: the ability to invade epithelial cells of the intestine, multiply intracellularly, and spread from cell to cell. All of the genes required for the invasion step are encoded on a large virulence-associated plasmid that is present in virulent strains of all species of Shigella as well as EIEC. These plasmids are functionally interchangeable with respect to expression of the invasion phenotype and share significant degrees of DNA homology (Sansonetti et al., 1985). Studies have focused on the 220 kb virulence plasmid of S. flexneri 2a. A 37 kb region of the invasion plasmid has been found to contain all of the genes necessary to permit the bacteria to penetrate into tissue culture cells. This DNA segment was identified as the minimal region of virulence plasmid necessary to allow a plasmid-cured derivative of *S. flexneri* (and *E. coli* K-12) to invade tissue culture cells (Maurelli et al., 1985). The nucleotide sequence of this part of the virulence plasmid from *S. flexneri*, as well as one from *S sonnei*, is known (see Galan et al., 1995 for summary; GenBank accession #D50601 for *S. sonnei*). The region encodes about 33 genes contained in two groups of genes transcribed in opposite orientation (FIG. 1*a*).

The 37 kb region of the virulence plasmid includes genes for invasion plasmid antigens (ipaBCDA) that encode the immunodominant antigens detected with sera from convalescent patients and experimentally challenged monkeys (Oaks et al., 1986). ipaB, ipaC and ipaD have been experimentally demonstrated to be required for invasion of mammalian cells (Menard et al, 1993). ipaA is also necessary and although an ipaA mutant shows about a 10-fold decrease in its ability to invade HeLa cells, internalization is not completely impaired in an ipaA mutant (Tran Van Nhieu, et al. 1997). The Ipa products are found associated with the outer membrane of Shigella and in culture supernatants. IpaB and IpaC form a complex on the bacterial cell surface and trigger a eukaryotic membrane ruffling process responsible for mediating entry via bacterium-directed phagocytosis (Menard et al., 1994; Adam et al., 1995; Menard et al., 1996; Parsot et al., 1995). Unlike other invasive pathogens, like Salmonella spp., Shigella spp. lyse the post-phagocytic endosomal membrane and multiply in the eukaryotic cell cytosol (Sansonetti et al., 1986). It is in the cytosol where Shigella develops the ability to spread intercellularly. The bacterium uses a protein polarly localized in the outer membrane, the IcsA protein, to direct the polymerization of host cell actin monomers that serve as a motor, propelling the bacterium within cellular protrusions, or fireworks, into adjacent uninfected cells (Bernardini et al., 1989 and Goldberg et al., 1993). Protrusion escape, which requires the lysis of two cellular membranes (that of the primary and secondarily infected cells), establishes the infection in neighboring cells and leads to bacterial spread across the colonic mucosa (Allaoui et al., 1992a).

To function in invasion and spread, the products of the ipa genes are secreted into the extracellular medium. Secretion occurs despite the lack of signal sequences for recognition found in the usual gram-negative bacterial transport system. Indeed, a growing number of animal and plant pathogens have been found to be similar to Shigella in the production of outer membrane or secreted virulence proteins which lack classical signal sequences. In spite of this diversity, the mechanisms utilized for bacterial virulence protein delivery are remarkably homologous. Research has shown that in Shigella Ipa protein secretion occurs via a dedicated transport apparatus composed of the gene products from another locus on the virulence-associated plasmid (FIG. 1*a*). The membrane expression of invasion plasmid antigens/surface presentation of Ipa antigens locus, called the mxilspa locus of Shigella, encodes 20 Mxi and Spa proteins, many of which have been demonstrated to be essential to Shigella virulence as measured in the Sereny test, invasion of and proliferation in cultured epithelial cell lines, plaque assay, or the binding of Congo red dye. Mxi/Spa proteins comprise the machinery necessary for secretion of the Ipa products (Andrews et al., 1991; Allaoui et al., 1992; Allaoui et al., 1993; Sasakawa et al., 1993) and define a unique system for protein secretion in pathogenic gram negative bacteria which is designated the type III secretion system.

The type III secretion systems are membrane bound, multicomponent structures responsible for the translocation of virulence effectors from the bacterial cytoplasm to either cell surface or intracellular eukaryotic targets (Hueck, 1998). Type III secretion is often referred to as contact-dependent, as it is induced by direct pathogen-host interaction. Additionally, expression of such systems can be induced at the transcriptional level by certain host conditions, including temperature and salt concentrations. Loci encoding varying groups of homologous type III secretory apparatus components have been identified, usually within large operons, in many mammalian and plant pathogens, including Shigella, Salmonella, Yersinia, enterohemorrhagic and enteropathogenic Escherichia coli, Pseudomonas, Burkholderia, Chlamydia, Bordetella, Xanthomonas, Ralstonia, and Erwinia. Several well conserved components of type III secretion systems are also similar to proteins involved in flagella biosynthesis, a finding which supports the theory that type III pathways arose from those responsible for flagellar subunit secretion. The loss of virulence in mxi-spa mutant strains of Shigella is generally attributed to failure of the type III secretion apparatus to secrete Ipa proteins.

Despite this growing body of knowledge, there is still a need in the art for the identity and function of the proteins involved in the entry and spread of pathogenic bacteria like Shigellae. There is also a need for systems to determine the intracellular expression requirements of the genes that encode proteins involved with entry and spread of such bacteria to facilitate the development of regimens for the diagnosis, prevention, and treatment of disease.

SUMMARY OF THE INVENTION

The present invention relates to our discovery that the mxiM protein of *Shigella flexneri* is indispensable for host cell entry and the spread of Shigella from cell to cell. Thus, the invention provides the mxiM protein or peptides or portions thereof as antigens in vaccines to prevent Shigella infections and treat hosts infected with Shigella by inhibiting intercellular spread. In another aspect, the invention relates to antibodies generated against the mxiM proteins, peptides, or portions thereof to detect Shigella in contaminated food and water supplies as well as in infected hosts. In yet another aspect, the invention relates to the DNA sequence of the mxiM gene or a fragment thereof to detect Shigella in contaminated food and water supplies as well as in infected hosts.

The present invention also describes a method called the TIER (test of intracellular expression requirements) for determining the intracellular expression requirements of genes and therefore, permitting one to establish the role of genes in the pathogenesis of organisms.

BRIEF DESCRIPTION OF THE DRAWINGS

FIG. 1*a* depicts the 220 kb virulence plasmid of *S. flexneri.*

FIG. 1*b* depicts the genetic organization of the mxi locus of Shigella spp. and homologies between its products and those of type III secretion systems from other pathogens.

FIG. 2 depicts the expression of mxiM in wild type and mxiM mutant strains.

FIG. 3 depicts the effect of the mxiM mutation on the expression and secretion of IpaB and IpaC.

FIGS. 4A and 4B depict the analysis of membrane fractions following sucrose density gradient centrifugation to determine the localization of mxiM in the inner or outer membrane.

FIG. 5(A) depicts the expression pattern of gfp (green fluorescent protein) from the P$_{LAC}$ (BS587-panels 1 and 2) and P$_{BAD}$ (BS586-panels 3 and 4) promoters (0 minute infection samples; panels 1 and 3 or 120 minutes post infection; panels 2 and 4). (B) depicts the cellular localization of IpaB expressed from the P$_{LAC}$ (BS580) and P$_{BAD}$ (BS579) promoters.

Figure 6:
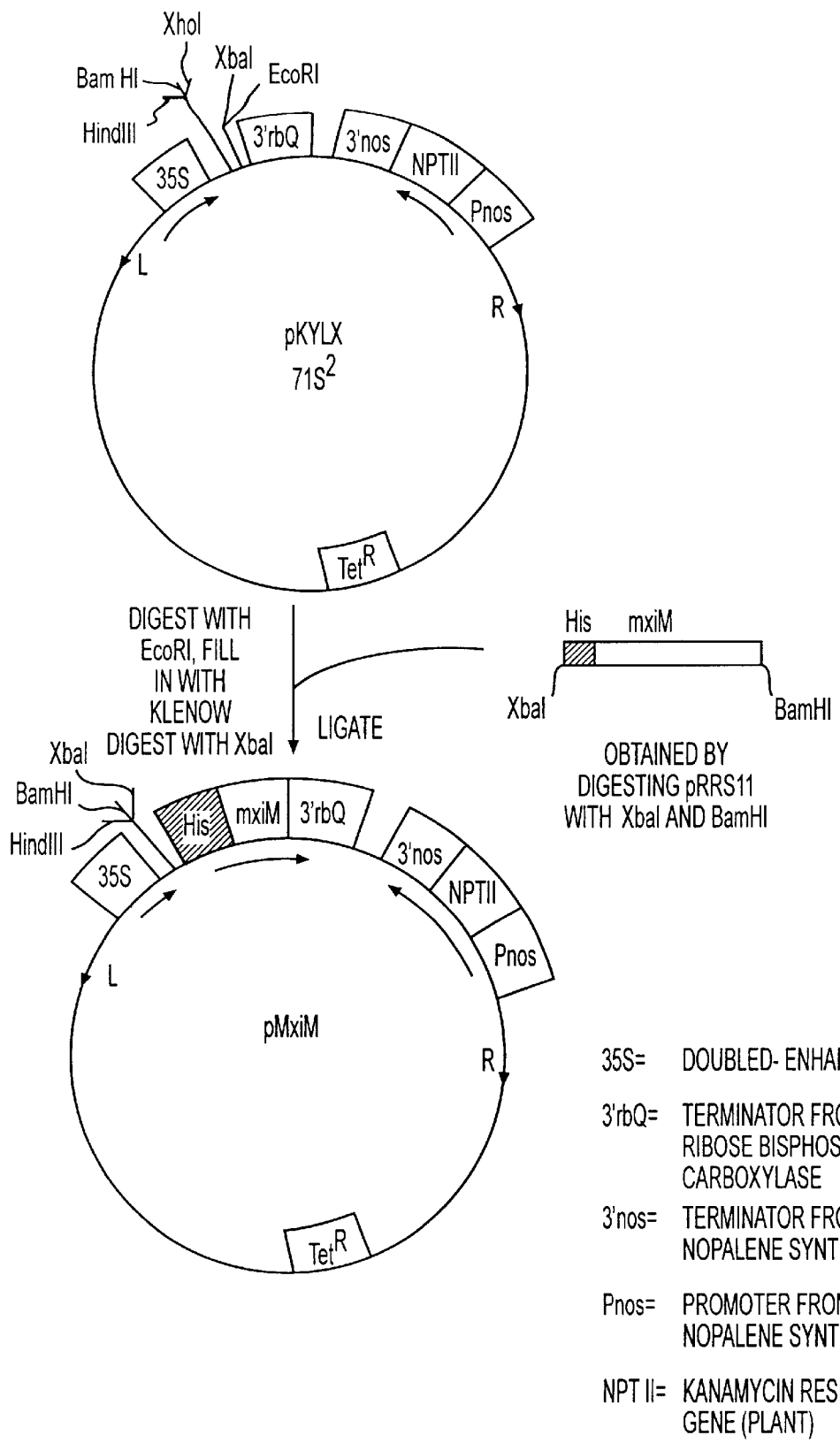

FIG. 6 depicts the pKLYX 71S$^2$ and pmxiM cloning vectors.

DETAILED DESCRIPTION OF THE INVENTION

The present invention relates to antigens, vaccines, and antibodies for use in the detection, prevention, and treatment of diseases caused by bacterial pathogens. By bacterial pathogens, we mean bacteria that infect and cause disease in plant and animal hosts such as humans or other mammals. Additional hosts include but are not limited to plants and animals of economic importance such as soybeans, tomatoes, papaya, citrus fruit, wheat, cows, pigs, and chickens as well as animals commonly kept as household pets. Examples of bacterial pathogens include Salmonella, Yersinia, enterohemorrhagic and enteropathogenic *Escherichia coli*, Pseudomonas, Burkholderia, Chlamydia, Bordetella, Xanthomonas, Ralstonia, Mycobacterium, Legionella, Erwinia, Shigella, and Listeria. In a preferred embodiment, the invention relates to detecting, preventing, and treating diseases caused by Shigella, the major etiological agent of bacillary dysentery, also known as shigellosis.

In a particularly preferred embodiment, the invention relates to a protein of Shigellae that we have found to be indispensable in the cell-to-cell spread of the bacteria. The significance of cell-to-cell spread is best understood in light of the process by which Shigellae invade the cells of the colonic mucosa.

Invasion by Shigellae is a multi-step process. The bacteria enter the cell using a variety of proteins including those that are encoded by genes on a large 220-kb plasmid. The plasmid contains a family of "invasion plasmid antigen" (ipa) genes whose products act at different stages in the pathogenic process.

Initially, the bacteria enter the cells by endocytosis, that is, the bacteria are taken up and internalized within a membrane-bound vesicle. The bacteria escape that vesicle, usually within 15 minutes, and enter the cytosol of the host cell. The bacteria induce formation of an actin-containing "tail" that drives the bacteria forward in spurts through the host cell's cytoplasm. During the bacterial movement, the bacteria are also replicating.

To move into adjacent cells, Shigellae form finger-like protrusions into the adjacent uninfected cells. The protrusions pierce the surface membrane of the adjacent cell and the bacteria are taken in, again in membrane-bound vesicles. As above, the vesicles are lysed, the bacteria escape into the cytoplasm, form a tail, and move through the cell while replicating.

None of these steps could occur but for the expression and secretion of the virulence products of the ipa genes. However, unlike most secreted products, the products of the ipa genes lack signal sequences. Thus, Shigellae have developed specialized secretion systems for the transport of these essential virulence products. The secretion of ipa proteins relies on a transport apparatus derived from the gene products of another locus on the virulence plasmid. This locus is called the membrane expression of invasive plasmid antigens/surface presentation of Ipa antigens, or "mxi/spa." The mxilspa genes and their products embody a system for secreting proteins, a system designated as a type III secretion system.

Figure 1B:
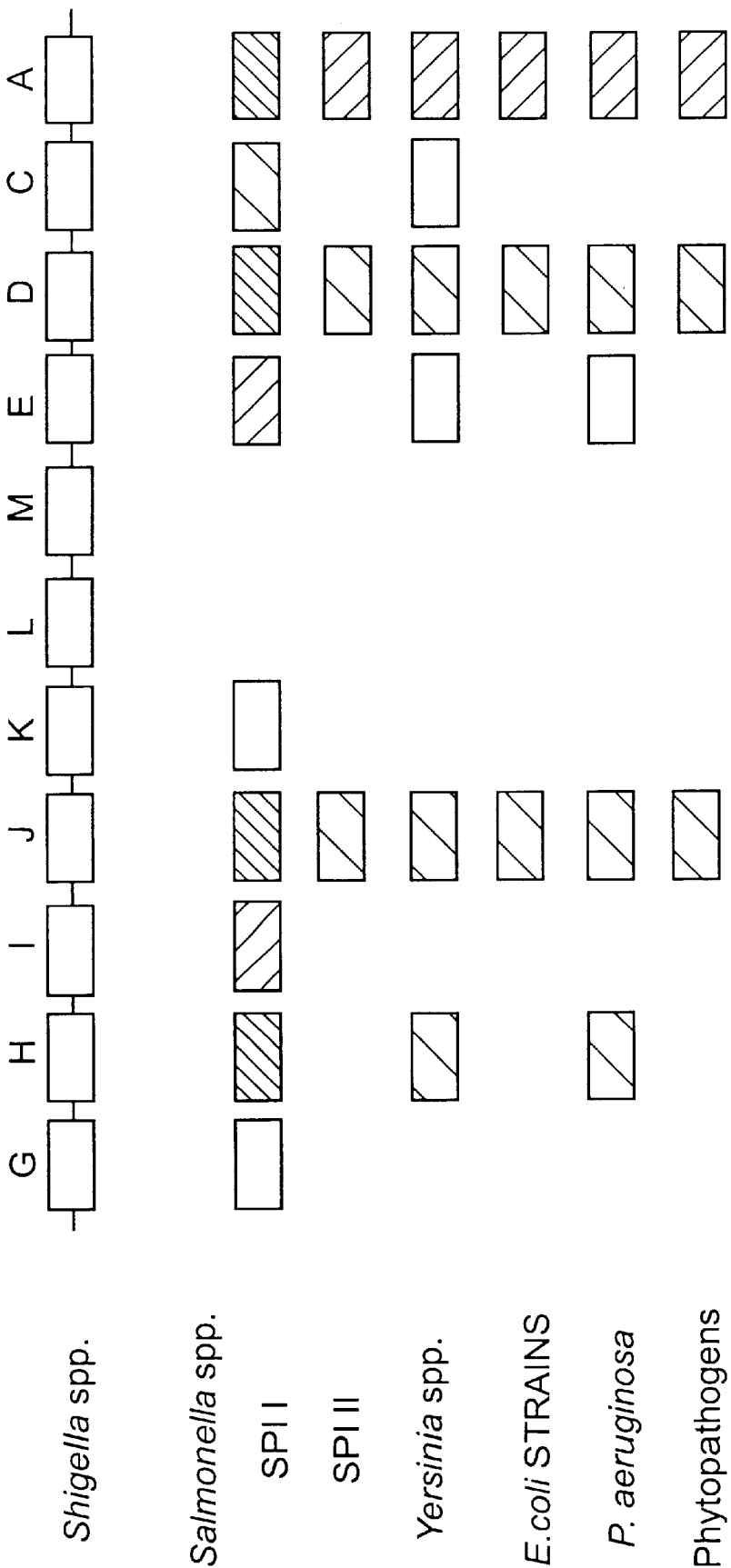

The mxi/spa locus encodes 20 Mxi and Spa proteins, many of which have been demonstrated to be essential for virulence. The present invention focuses on one of the seven mxi-spa genes (mxiH, I, K, L, M, E, and C) that were uncharacterized with respect to their roles in Ipa secretion and invasion (Menard et al., 1996). Most of these genes are predicted to encode type III secretory subunits based on protein sequence similarities to elements of homologous type III pathways from other pathogens (FIG. 1B).

However, the protein products of mxiL and mxiM appear to be unique as set forth below and may, therefore, serve a function specific to Shigella. The mxiM gene has been sequenced, but was uncharacterized with respect to its role in Shigella pathogenesis and its mechanism of function (Allaoui et al., 1992). In addition, mxiM has been previously shown to encode a lipoprotein. Lipoproteins have been identified as necessary components of the general secretory pathway of Gram-negative bacteria (Hardie et al., 1996) as well as several type III secretion systems (including MxiJ of the Shigella Mxi-Spa pathway) (Allaoui et al., 1992). Bacterial lipoproteins have also been identified as essential elements of a variety of transmembrane traffic systems. Thus, we undertook a study to determine the role of mxiM.

To fully characterize mxiM, we developed a novel system to study its role intracellularly. The TIER (test of intracellular expression requirements) system tests the role of genes in the pathogenesis of organisms. A preferred embodiment of the invention is to test the intracellular expression requirements of Shigella invasion genes. We have determined that mxiM of Shigella flexneri is an indispensable type III secretion component, required for both Ipa translocation, and invasion. Using the TIER system, we have determined that mxiM is required for intercellular spread. In a similar fashion, we have determined that IpaB, IpaC, IpaD, VirF, VirB, and Spa33 are required for post-invasion cell-to-cell spread. Genes such as ipa, mxi and spa, that are important in the pathogenesis or life cycle of the organism are, therefore, targets for prevention and therapy.

For the purposes of this application, "mxiM" refers to the gene designation, and "mxiM" refers to the protein designation. As set forth in Allaoui, A., Parsot, C. R. and Sansonetti, P. J., "MxiJ, a lipoprotein involved in secretion of Shigella Ipa invasins, is homologous to YscJ, a secretion factor of the Yersinia Yop proteins," J. Bacteriol. 174, 7661–7669 (1992) (incorporated herein by reference), the mxiM nucleotide sequence (in bold) is shown below and the mxiM amino acid sequence with the single letter amino acid designation follows:

```
SEQ ID NO: 1 (GenBank Accession #M98391)
  1 TTAATTAGTG TCTTTGAAGC AGGGAGAGAG GCAGATGATT CGACATGGTA GTAATAAGTT
 61 GAAAATATTT ATTTTAAGTA TATTGCTATT AACACTGAGT GGGTGTGCTT TAAAGTCATC
121 ATCTAATTCT GAAAAAGAAT GGCATATTGT TCCTGTAAGT AAGGATTATT TTTCTATTCC
181 AAATGATTTA TTATGGTCGT TTAATACAAC CAATAAAAGT ATAAATGTTT ACTCTAAATG
```

-continued

```
241 TATTAGTGGT AAGGCGGTTT ATAGTTTTAA TGCAGGTAAA TTCATGGGCA ACTTTAATGT

301 TAAGGAAGTA GATGGGTGCT TCATGGATGC ACAAAAGATA GCTATAGATA AACTATTTTC

361 TATGCTGAAA GACGGGGTTG TTTTAAAAGG TAATAAGATA AATGATACCA TCCTTATAGA

421 GAAGGATGGG GAAGTTAAAT TAAAATTAAT TCGAGGGATA TAATTGTATT GTGAGTAAAT

481 ATAAAGGTCT AAATACAAGT AATATGTTTT ACATTTACTC TAGTGGACAT GAACCAGTTA

541 ACGTTGAGCT TGTAAAAGAT AAAGAACGTA ACATAATTGA GCTGGCTCCA GCATGGAAGG
```

```
SEQ ID NO: 2 (GenBank Accession #M98391)
    MIRHGSNKLK IFILSILLLT LSGCALKSSS NSEKEWHIVP VSKDYFSIPN DLLWSFNTTN

KSINVYSKCI SGKAVYSFNA GKFMGNFNVK EVDGCFMDAQ KIAIDKLFSM LKDGVVLKGN

KINDTILIEK DGEVKLKLIR GI
```

In one aspect of the present invention, the TIER system involves generating DNA constructs containing a gene of interest from a pathogen cloned into expression vectors, creating mutant pathogens by inactivating the endogenous copy of the gene of interest, transforming the mutant pathogens with the DNA constructs, infecting the appropriate cells with the transformed pathogens, and assaying for gene function.

DNA constructs are generated by using cloning methods well known in the art to clone the gene of interest into two expression vectors. One expression vector contains at least one constitutive promoter while the second vector contains at least one inducible/repressible promoter. A preferred embodiment is to use the $P_{LAC}$ promoter of pBluescript (without an intact lacI gene) and the PBAD promoter (arabinose induction and glucose repression) of pBAD18. The pBAD18 vector also encodes the araC gene which mediates the induction/repression of the $P_{BAD}$ promoter. Shigella genes under the control of the $P_{BAD}$ promoter are specifically repressed upon removal of arabinose from the medium.

The endogenous copy of the gene of interest is inactivated by known methods including deletions, insertions, point mutations, recombinations, etc. However, inactivation must be carried out in a manner such that surrounding genes are not affected. For example, non polar mutations only affect the gene of interest and not the transcription and translation of downstream genes.

Using any one of the known methods of transformation, pathogens with an inactive endogenous gene of interest are transformed with the DNA constructs generated above and used to infect the appropriate cell type. Suitable assays specific for the gene of interest will determine if the gene is necessary for pathogenesis. In this application, we transformed *Shigella flexneri* with $P_{LAC}$ and $P_{BAD}$ constructs expressing mxiM and IpaB. The transformed bacteria were assayed for Congo red binding, Ipa secretion, and used to infect fibroblast monolayers to measure cell invasion and intercellular spread.

To illustrate the power and utility of the TIER system, we created a mxiM mutant (allele designation mxiM1) of wild type *S. flexneri* 2457T by insertionally inactivating the endogenous copy of mxiM using an aphA-3-kanamycin resistance cassette as set forth in Example I and Table 1. We showed that the mxiM1 mutant, BS547, lost the ability to invade semi-confluent L2 cells, spread intercellularly, bind Congo red dye, and secrete IpaB and IpaC. Thus, this mutant of *S. flexneri* was avirulent. However, complementation with wild type mxiM from plasmid pRRS5 (Table 1) in strain BS547 restored Congo red binding, invasion, cell-to-cell spread, and IpaB and IpaC secretion to the mutant. The results demonstrate that the mxiM1 mutant allele had no polar effects on the transcription and translation of the downstream genes of the mxi operon.

mxiM1 mutant strains BS548 and BS575 expressing mxiMfrom the $P_{BAD}$ and $P_{LAC}$ promoters, respectively, were used in the TIER system to test for the intracellular requirements of mxiM. Genes under the control of the $P_{LAC}$ promoter of pBluescript are constitutively expressed, while genes under the control of the $P_{BAD}$ promoter are inducible/repressible by arabinose/glucose. Any gene expressed from $P_{BAD}$ will be shut off after removal of arabinose from the medium.

When grown in the presence of arabinose, strain BS548 carrying $P_{BAD}$-mxiM was able to bind Congo red, secrete IpaB and IpaC protein, and invade L2 cells. However, strain BS548 was unable to spread intercellularly and form plaques in the absence of exogenous arabinose in the culture medium during the plaque assay. Therefore, $P_{BAD}$-mxiM is capable of supporting invasion but not intercellular spread. When mxiM was expressed from the constitutive $P_{LAC}$ promoter in strain BS575, no defects were observed and the mxiM mutant behavior was fully complemented back to wild type.

Using the TIER system, we have demonstrated the importance of mxiM in the pathogenesis of *S. flexneri*. We also used ipaB, ipaC, and ipaD mutants of *S. flexneri* (Menard et al., 1993), as well as virF (Sakai et al., 1986), virB (Adler et al., 1989), and spa33 (Schuch and Maurelli, unpublished data) and found that each gene is essential for post-invasion steps. Thus, one aspect of the TIER system is to identify genes from pathogens that are necessary for pathogenesis.

Having identified mxiM as necessary for intercellular spread, using the TIER system, our invention also includes use of the protein, its peptides, portions thereof (a portion being less than and/or other than a peptide and specifically includes epitopes) for diagnosing, preventing, or treating diseases caused by Shigella. Thus, in one aspect, the invention also relates to the treatment of a patient by administration of an immunostimulatory amount of the vaccine. A patient is hereby defined as any person or non-human primate in need of immune stimulation, or to any subject for whom treatment may be beneficial. An immunostimulatory amount refers to that amount of vaccine that is able to stimulate the production of antibodies directed against the mxiM protein, peptides, and portions thereof, including the immunogenic epitope. Preferably, an immunostimulatory amount refers to that amount of vaccine that is able to stimulate an immune response in a patient which is sufficient to prevent, ameliorate, or otherwise treat disease caused by pathologic bacteria such as Shigella.

As would be understood by those of ordinary skill in the art, prevention refers to the blocking of infection or clinical disease; amelioration means a reduction in the number or severity of symptoms such as dysentery and treatment refers to the elimination of bacteria or interference with their ability to cause disease. In another aspect of the invention, the vaccines function by inhibiting or reducing intercellular spread, as can be measured by the methods known in the art and/or set forth herein, such as the inhibition of plaque formation.

The invention also encompasses secondary booster immunizations that may be given at intervals ranging from one week to many months later. The dosage of the primary and secondary inocula can be readily determined by those of ordinary skill in the art, but an acceptable range is 0.01 µg to 100 µg per inoculum. The amount to be administered and the frequency of administration can be determined empirically and will take into consideration the age and size of the patient being treated and the stage of the disease (e.g., prior to bacterial exposure, early in the disease process, or after full blown shigellosis).

Treatment comprises administering the immunogenic composition by any method familiar to those of ordinary skill in the art, including intravenous, intraperitoneal, intracorporeal injection, intra-articular, intraventricular, intrathecal, intramuscular, subcutaneous, topically, tonsillar, intranasally, intravaginally, and orally. The preferred methods of administration are intravenous, intramuscular, intranasal, oral, and subcutaneous injections. The composition may also be given locally, such as by injection into the particular area, either intramuscularly or subcutaneously.

As used herein, a vaccine, or pharmaceutical composition, comprises at least one immunological composition, preferably dissolved or suspended in a pharmaceutically acceptable carrier or vehicle. Any pharmaceutically acceptable carrier can be employed for administration of the composition. Carriers can be sterile liquids, such as water, oils, including petroleum oil, animal oil, vegetable oil, peanut oil, soybean oil, mineral oil, sesame oil, and the like. With intravenous administration, the constructs are preferably water soluble and saline is a preferred carrier. Aqueous dextrose and glycerol solutions can also be employed as liquid carriers, particularly for injectable solutions. Suitable pharmaceutical carriers are described in *Remington's Pharmaceutical Sciences*, 18th Edition (A. Gennaro, ed., 1990) Mack Pub., Easton, Pa., incorporated by reference. The immunological composition may also be formulated with solubilizing agents, emulsifiers, stabilizers, flavorants, adjuvants, carriers and other components.

In another embodiment of the invention, the vaccine of the invention is a plant cell that has been transformed with a vector encoding the mxiM protein, peptides, and portions thereof in such a way that the transformed plant expresses the protein, peptide, or portion thereof. A general description of this is set forth in U.S. Ser. No. 08/840,466 (filed on Apr. 18, 1997) (which is herein incorporated by reference). In this embodiment, the plant, or a part thereof, is administered to a patient. This aspect of the invention also relates to a DNA construct that codes for the expression of a heterologous DNA in a plant, wherein the heterologous DNA encodes mxiM, peptides, or portions thereof.

Plant cells have successfully been engineered to express heterologous genes, such as those of bacterial origin. Crop plants of all types have been engineered with genes from bacterial origin. Some examples of these are the commonly-used antibiotic resistance genes, such as the scorable marker genes for neomycin phosphotransferase (NPTII) and hygromycin phosphotransferase (HPII). These genes were isolated from the bacterium *E. coli* (Fraley, R. T., et al., Proc. Natl. Acad. Sci. USA 80: 4803 (1983); Vandenberghe et al., Plant Mol. Biol. 5: 299 (1985)). Another popular scorable marker gene routinely used in plant transformation studies also comes from *E. coli*: beta glucuronidase (GUS) (Jefferson Plant Mol. Biol. Rep. 5: 387–405 (1988)). All of these genes have been useful and have been highly expressed by transgenic plants, i.e., those containing heterologous DNA, in their native form; they required no modifications in their coding sequence.

Other genes from bacteria, however, have been poorly expressed when engineered into plants. One example is the mercuric ion reductase gene from *E. coli* (Clayton et al., 1996, Mecuric ion reduction and resistance in transgenic *Arabidopsis thaliana* plants expressing a modified bacterial merA gene). It required modification in its coding sequence before it could be expressed. Perhaps the best-known example are insecticidal cry genes from *Bacillus thuringiesis*. They have all exhibited low to no expression until they were "rebuilt" or codon optimized for expression in plants (Perlak et al., Proc. Natl. Acad. Sci. USA 88: 3324–3328 (1991); Adang et al., Plant Mol. Biol. 21: 1131–1145 (1993)). In these studies, researchers reconstructed the genes by synthesizing and linking oligonucleotides that encode preferential codons for the plant species, without changing the amino acid sequence. By matching the codon usage of the new gene to plant-preferred codons, the introduced gene can be highly expressed (e.g., Stewart et al., Insect control and dosage effects in transgenic canola, *Brassica napus* L. (Brassicaceae), containing a synthetic *Bacillus thuringiensis* CryIa(c) gene. Plant Physiology, 112:115–120 (1996)). Thus, the expression of bacterial genes by plant cells has been accomplished.

Plants engineered with a foreign gene have been successful delivery agents for oral vaccines. As set forth in a recent review, (Mason and Arntzen, Tibtech 13: 388–392 (1995)), the art has recognized such uses of engineered plants. The body of work also includes the recent demonstration that, when expressing genes that code for antigens of viral and bacterial pathogens in plants, the antigens retain their immunogenic properties (Mason and Arntzen, Tibtech 13: 388–392 (1995)). Mason et al. (Mason et al, Proc. Natl. Acad. Sci. USA 89: 11745–11749 (1992)) introduced the concept of engineering plants as a vehicle delivery system for vaccines and have since shown that their system is effective for hepatitis B (Thanavala et al., Proc. Natl. Acad. Sci. 92: 3358–3361 (1995)), *E. coli* enterotoxin B subunit and cholera-toxin B subunit (Haq et al., Science 268: 714–716 (1995)). One basis for the effectiveness of this strategy rests on the fact that the antigens stimulate mucosal immunity.

Using a similar approach, a skilled artisan may express mxiM or, for example, mxiM as a fusion protein with one or more other antigens, in the tobacco plant or other plants, such as carrots, bananas, canola, and alfalfa, and potatoes. Other monocotyledonous and dicotyledonous plants within the scope of the invention include soybean, sunflower, alfalfa, banana, coconut, pineapple, corn, wheat, oats, rye, barley, rice, canola, carrots, tobacco, peanuts, cotton, sweet potato, potato, cassava, coffee, citrus, cocoa, tea, avocado, fig, guava, mango, olive, papaya, cashew, macadamia, almond, sugar beet, tomato, lettuce, green bean, lima bean, pea, *cucumis, cantalupensis*, musk melon, azalea, hydrangea, hibiscus, roses, tulips, daffodils, petunias, carnation, poinsettia, chrysanthemum, and conifers. When such transformed plants or portions thereof are fed to patients, such as children, the transformed plants express the mxiM protein or a fusion protein, thereby delivering the antigens to the patients, in order to stimulate an immune response. Such a method is desirable in that it is an inexpensive and efficient method for protecting the patients. Moreover, protecting against future colonization by human pathogens such as Shigella reduces the risk of infection for humans.

In one transformation procedure, the mxiM gene is put under the control of a constitutive plant promotor in an *Agrobacterium tumefaciens* binary vector and the plants are engineered by Agrobacterium-mediated transformation.

In another embodiment of this invention antibodies specific for mxiM can be used for passive immunization, for example, by application to the colonic mucosa. In this example, the transformed plant is fed directly to animals such as cattle such that the mxiM protein (including peptides and portions thereof) is expressed in the host organism. Administration of the plant host to cattle stimulates an immune response to mxiM and any other antigens expressed by the plant cell. Antibodies produced by the animal will be found in animal products such as milk and can be used to passively immunize humans as well as nonhuman primates. Monoclonal antibodies are preferred for this application. Any of the compositions of the invention may be used to generate antibodies against mxiM.

The term "antibodies" is meant to include polyclonal antibodies, monoclonal antibodies, fragments thereof such as F(ab')2, and Fab fragments. Antibodies are defined to be specifically binding if they inhibit at least one biological activity of mxiM, for example, in the secretion of Ipas. Alternatively, an antibody specifically binds if it is displaceable in an ELISA or comparable immunological assay. Affinities of antibodies can be readily determined using conventional techniques, for example those described by Scatchard et al., Ann. N.Y Acad. Sci., 51:660 (1949).

Monoclonal antibodies specific for mxiM can be readily prepared using well-known procedures, see for example, the procedures described in U.S. Pat. Nos. RE 32,011, 4,902, 614, 4,543,439, and 4,411,993*; Monoclonal Antibodies, Hybridomas: A New Dimension in Biological Analyses*, (Kennett, McKeam, & Bechtol eds., 1980), Plenum Press. When used for treating human patients, it is desirable to replace potentially antigenic non-human portions of the antibody with human sequence. A hybrid molecule may be generated in which only the antigen-specific variable, or complementary determining region (CDR) is composed of non-human sequence. These humanized antibodies are thus particularly preferred for clinical use. See, for example, LoBuglio et al., Proc. Natl. Acad. Sci. USA 86:4220–24 (1989); Meredith et al., J. Nucl. Med. 33, 23–29 (1992); Salah et al., Hum. Antibod. Hybridomas 3:19–24 (1992); Knight et al., Mol. Immunol 32:1271–81 (1995); and Lockwood et al., Q.J. Med. 89:903–12, (1996).

Various strategies for designing these humanized antibodies are reviewed in Winter and Milstein, Nature 349:293–99 (1991); Harris, BCSTBS5 23(4):1035–38 (1995); S. Morrison and J. Schlom, *Important Advances in Oncology* (1990), J.B. Lippincott Co.; L. Presta, Humanized Monoclonal Antibodies, in *Annual Reports in Medicinal Chemistry* (1994) Academic Press; and A. Lewis and J. Crowe, Generation of Humanized Monoclonal Antibodies by 'Best Fit' Framework Selection and Recombinant Polymerase Chain Reaction, in *Generation of Antibodies by Cell and Gene Immortalization*, Year Immunol. Vol. 7, pp. 110–18 (C. Terhorst, F. Malvasi, & A. Albertini eds., 1993), each of which is incorporated herein by reference.

Polyclonal antibodies can be readily generated from a variety of sources, for example, horses, cows, goats, sheep, dogs, chickens, rabbits, mice, or rats, using procedures that are well-known in the art. In general, purified mxiM is administered to a host animal typically through parenteral injection. The immunogenicity of mxiM can be enhanced through the use of an adjuvant, for example, Freund's complete or incomplete adjuvant. Following booster immunizations, small samples of serum are collected and tested for reactivity. Examples of various procedures and assays useful for the preparation and analysis of polyclonal and monoclonal antibodies are well known in the art and include those described in the series by P. Tijssen, *Laboratory Techniques in Biochemistry and Molecular Biology: Practice and Theory of Enzyme Immunoassays*, (Burdon & van Knippenberg eds., 3rd ed., 1985) Elsevier, New York; and *Antibodies: A Laboratory Manual*, (Harlow & Lane eds., 1988), Cold Spring Harbor Laboratory Press; as well as procedures such as countercurrent immuno-electrophoresis (CIEP), radioimmunoassay, radio-immunoprecipitation, enzyme-linked immuno-sorbent assays (ELISA), dot blot assays, and sandwich assays, see U.S. Pat. Nos. 4,376,1 10 and 4,486,530, all of which are incorporated herein by reference.

In another aspect, the invention provides a means for rapidly detecting the presence of Shigella in clinical samples, such as stool samples, and in environmental samples, such as food or water, by detecting the presence of the mxiM protein or portions thereof. The speed of the method results in part from the use of antibodies to mxiM which avoids the time-consuming process of culturing the bacteria. The use of mxiM antibodies, as described above, also makes the detection method highly sensitive and relatively safe for the user. In addition, the detection method is highly specific to Shigella because of the uniqueness of mxiM to Shigella.

The antibodies of the invention may be monoclonal or polyclonal, although monoclonal antibodies are preferred. In addition, the use of antibodies permits the ready addition of other antibodies so that the method can detect the presence of other pathogenic bacteria such as, for example, enterohemorrhagic *Escherichia coli* (EHEC).

A general description of such methods is provided in U.S. Pat. No. 5,747,272. In the practice of one aspect of the invention, samples are spotted onto a substrate. While any appropriate substrate may be used, in a preferred embodiment, the invention uses nitrocellulose membrane and, more preferably, in a dot blot apparatus connected to a vacuum. The substrate is air dried and then incubated in a solution containing a biological detergent and a blocking agent capable of blocking nonspecific binding sites. The solution such as phosphate buffered saline with 0.1% TWEEN® 20 (PBS-T) and 5% non-fat dry milk may be used. After an appropriate period of incubation, the substrate is washed to remove excess blocking agent.

The substrate is next incubated in a mixture of the antibodies specific for the pathogen to be detected. In a preferred embodiment, at least one antibody is directed to the mxiM protein or portions thereof of *S. flexneri* 2a. In a more preferred embodiment, the anti-mxiM antibody is a monoclonal antibody. The substrate is incubated for a time sufficient to allow the one or more antibodies to bind to any bacteria which may be present in the samples. Dilutions of the antibodies in phosphate buffered saline ranging from 1:2 to 1:64 are generally sufficiently sensitive for the purposes described herein.

After an appropriate incubation time, the antibody mixture is removed and the substrate is washed to remove any remaining antibodies which have not bound to the samples. The samples are then assayed for the presence of bound antibodies using any method familiar to those of ordinary skill in the art. Among the methods are Western blotting techniques or ELISA developed with an enhanced chemiluminescent compound such as horseradish peroxidase or alkaline phosphatase or by colorimetric detection (Sambrook et al, 1989).

In a preferred embodiment, the chemiluminescent detection reagent is a solution of a chemiluminescing compound, an oxidant and a sensitivity enhancer. In the presence of a peroxidase enzyme which is conjugated either to a secondary antibody or directly to the previously described antibodies, the chemiluminescing compound is oxidized to an excited state, which emits a measurable amount of light when returning to a non-excited state. In order to produce the requisite sensitivity for the detection of low to moderate amounts of Shigella, a sensitivity enhancer may be included in the detection reagent.

The chemiluminescent reaction is a peroxidase-catalyzed reaction of an oxidant and a chemiluminescent compound. In ELISAs, the peroxidase enzyme is conventionally a horseradish peroxidase enzyme which has been conjugated to an anti-mouse immunoglobulin antibody. However, other peroxidases, particularly plant peroxidases, may be substituted.

Chemiluminescent compounds are generally described as being 2,3-dihydro-1,4-phthalazinedione (DPD) compounds capable of emitting light through the previously described oxidation reaction. The most commonly used DPD compounds are luminol (5-amino-2,3-dihydro-1,4-phthalazinedione) and isoluminol (6-amino-2,3-dihydro-1, 4-phthalazinedione).

Solutions containing chemiluminescent DPD compounds, alone, are not sufficiently sensitive to detect low, but clinically significant, amounts of Shigella in samples. The sensitivity of chemiluminescent reaction may therefore be enhanced by the addition of a phenol or naphthol having a general formula as described in U.S. Pat. No. 4,598,044, incorporated herein by reference, at column 2, line 37 through column 3, line 3 and column 4, lines 28–45. The described phenols and naphthols capable of enhancing the sensitivity of the chemiluminescing reaction are hereinafter referred to as sensitivity enhancers.

The oxidant will be selected for its ability to react with the predetermined DPD compound, resulting in the emission of light. Commonly used oxidants include hydrogen peroxide and solutions containing perborate ion.

In a preferred embodiment, the substrate is incubated in a solution containing a secondary antibody which has been conjugated to a peroxidase enzyme as a label. The secondary antibody is allowed to bind to any anti-mxiM antibody present on the membrane. The sample is then washed to remove unbound secondary antibody. The membrane is immersed in a detection reagent, such as the reagents set forth above. Using the chemiluminescent reagents, the amount of bound antibody is measured by detecting the luminescence of the sample.

Western blotting techniques using a chemiluminescent label are preferred as a rapid, highly sensitive and non-radioactive assay. After exposure to the antibody of the invention, the substrate is incubated in a horseradish peroxidase-conjugated anti-mouse immunoglobulin G antibody and then washed to remove any unbound antibody. The substrate is then immersed in a detection reagent containing an oxidant, a chemiluminescing compound and a phenolic enhancer.

After immersion, the membrane is immediately exposed to a photographic film capable of detecting the light emitted from the peroxidase catalyzed reaction of the detection reagent. The exposure time is dependent upon the film used but generally will range from approximately 10 second to 3 minutes. The presence of antigen can then be detected when the film is exposed. Other methods of detection may use a photodetector cell to detect emitted light.

Physiologically buffered saline solutions, biological detergents and blocking agents capable of blocking nonspecific binding sites are all well known to the art, and practioners will readily appreciate that a wide range of combinations could be substituted for preferred solution without significantly affecting the sensitivity of the assay. For example, bovine serum albumin (BSA) may be substituted for nonfat dry milk as a blocking agent. Similarly, borate, carbonate, acetate, and Tris [tris (hydromethyl) aminomethane)] could be substituted for phosphate as a buffer. Further, any biological detergent generally having similar properties to TWEEN® 20 may be substituted. The chemiluminescent reaction will generally occur over a range of pH from 6 to 10, but preferably would be within a range of pH 7–9.

Enzyme-linked Immunosorbent Assays (ELISAs) are generally-known means of assaying for the presence of antigens in test material. Those familiar with the art will readily appreciate that the invention described herein may be adapted to other conventional ELISA techniques. For example, the peroxidase enzyme may be conjugated directly to the antibodies against mxiM. In such case, the use of an anti-mouse secondary antibody would be omitted.

The invention also includes kits to carry out the method described above. Conventionally, the kits would include the anti-mxiM antibodies, a substrate on which to perform the assay, wash solutions, a secondary antibody capable of binding the previously-described antibodies and which is conjugated to a peroxidase enzyme, and film or other means for detection and instructions for the use of the kit. In such a conventional kit, the antibody mixtures and all reagents would be provided in standardized dilutions, such that the user would need only to prepare the sample, including serial dilution (if desired), and proceed with the assay according to the directions provided.

In the preferred embodiment, the chemiluminescent reaction will occur adequately at normal room temperatures. Accordingly, no special apparatus or facility will normally be required for temperature maintenance when using the kit.

Although the description and example of the invention provided herein demonstrate a simple kit for detection of Shigella in food or clinical samples, those familiar with art will readily understand that other forms of the kit will allow the user to detect the relative quantity of bacteria contained in a sample. By way of example, such a kit may use a means for measuring the amount of light emitted by the chemiluminescent assay of a clinical sample, or the kit may provide for the assay of a sample culture against one or more series of cultures having predetermined quantities of antigen.

In another embodiment, the invention relates to the DNA sequence of the mxiM gene or a fragment thereof to detect Shigella in contaminated food and water supplies as well as in infected hosts.

In yet another embodiment, the modified strains of *S. flexneri* described herein provide an excellent vehicle for gene delivery (Sizemore et al., 1995 and 1997) and ultimately vaccine production. Vehicles for gene delivery are not limited to *S. flexneri* or mxiM mutants of *S. flexneri*. Genes can also be introduced by other modified bacteria such as Salmonella, *E. coli*, etc. By modified, we mean bacteria that can invade but not cause disease or spread resulting in cell damage. Any bacterial pathogen with a mutated copy of a gene that was determined by the TIER system to be necessary for post-invasion events such as intracellular multiplication and intercellular spread but not invasion, will also be useful as a gene delivery vehicle. Examples include genes whose expression may be required for toxin synthesis, cell-to-cell spread, and intracellular multiplication. These examples, however, do not include all possible post invasion requirements of virulence gene expression of potential bacterial gene delivery vehicles. Mutation of such genes would enhance the safety of the delivery vehicle without altering the ability of the vehicle to invade target cells.

A second class of virulence genes would include genes whose expression is required both for invasion and for post invasion events. An example of such a gene is mxiM and is described as follows. The endogenous copy of the mxiM gene would be mutated in the bacterial delivery vehicle and complemented with a copy of the wildtype mxiM gene cloned into a pBAD18 expression vector or a similar vector using an inducible/repressible promoter. Expression of mxiM from the pBAD18 expression vector would permit invasion to occur. Repression of mxiM gene expression from the pBAD18 expression vector after entry into the eukaryotic cell in the absence of exogenous arabinose would block essential post invasion events, in this example, cell-to-cell spread. This process thereby attenuates the bacteria and improves safety of the bacterial gene delivery vehicle.

The gene(s) to be delivered can be any piece of DNA encoding a full length peptide or fragments thereof. The gene to be delivered may include all DNA sequences necessary for proper expression and protein modification such as splice acceptor/donor sites, poly A signals, signal peptides (for secretion, post-translational modifications, etc.), etc. The DNA can be subjected to mutagenesis without changing the immunogenicity or activity of the gene product. Such a vaccine gene can be cloned by known methods into a separate expression vector or the same expression vector carrying the $P_{BAD}$-mxiM construct. The mxiM1 mutant strain of Shigella bearing the $P_{BAD}$-mxiM construct is able to infect colonic epithelial cells and express the gene of interest which will ultimately lead to antibody production against the protein product from the gene of interest. In addition, the mxiM mutation of Shigella attenuates the organism's virulence due to its inability to spread from cell to cell. Thus, the mutant Shigella organisms are safe and provide a safe and specific vehicle for gene delivery.

The following examples are presented to promote a fuller understanding of this invention. These examples do not, however, limit the scope of the invention.

EXAMPLE I

Materials and Methods
1. Construction of mxiM Mutant Plasmids and Bacterial Strains The mxiM locus of the mxi operon was uncharacterized with respect to its role in Shigella pathogenesis, yet it was of particular interest to us since mxiM encodes a lipid-modified protein (Allaoui et al., 1992). Lipoproteins have been identified as integral components of DNA secretion (Baron et al., 1997) and uptake systems (Fussenegger et al., 1996), the general secretory pathway of Gram-negative bacteria (Hardie et al., 1996), type IV pilus assembly (Ramer et al., 1996), as well as several type III secretion systems (including MxiJ of the Shigella Mxi-Spa pathway) (Allaoui et al., 1992). We thus undertook studies to determine whether mxiM was essential for Shigella virulence. *S. flexneri* strains and plasmids used in this study are described in Table 1.

TABLE 1

Bacterial strains and plasmids.

| Strain/Plasmid | Relevant genotype/phenotype | Source/Reference |
|---|---|---|
| Strain | | |
| 2457T | Wild-type *S. flexneri* serotype 2a | Formal et al. (1958) |
| M90T | Wild-type *S. flexneri* serotype 5 | Sansonetti et al. (1982) |
| BS473 | 2457T strep$^R$ | Maurelli Lab Stock |
| BS547 | 2457T mxiM1 (mxiM::aphA-3) | Schuch and Maurelli (1999) |
| BS548 | BS547/pRRS4 (mxiM1/P$_{BAD}$-mxiM$^+$) | Schuch and Maurelli (1999) |
| BS567 | M90T ipaB2 (ipaB::aphA-3) | Ménard et al. (1993) |
| BS575 | BS547/pRRS5 (mxiM1/P$_{LAC}$-mxiM$^+$) | Schuch and Maurelli (1999) |
| BS576 | BS547/pBAD18 | Schuch and Maurelli (1999) |
| BS577 | 2457T ΔicsA (P$_{BAD}$-icsA$^+$) | Maurelli Lab Stock |
| BS579 | BS567/pRRS7 (ipaB2/P$_{BAD}$-ipaB$^+$) | This work |
| BS580 | BS567/pRRS8 (ipaB2/P$_{LAC}$-ipaB$^+$) | This work |
| BS586 | 2457T/pRRS9 (P$_{BAD}$-gfp) | This work |
| BS587 | 2457T/pRRS10 (P$_{LAC}$-gfp) | This work |
| BS588 | BS547/pBluescript SK$^+$ | Schuch and Maurelli (1999) |
| Plasmid | | |
| pATM349 | Expression vector encoding a GFP red-shifted mutant (GFPmut2) | Cormack et al. (1996) |
| pBAD18 | arabinose-inducible P$_{BAD}$ expression vector | Guzman et al. (1995) |
| pET19b | vector used to construct histidine-tagged MxiM | Novagen |
| pGP704 | suicide vector used to disrupt mxiM | Miller and Mekalanos (1988) |
| pRRS1 | An 1850 bp PCR generated fragment, extending from 912 bp upstream of the mxiM start codon to 511 bp downstream of the stop codon, was ligated with EcoRI-HindIII digested pUC19 | Schuch and Maurelli (1999) |
| pRRS2 | The 840 bp SmaI fragment of pUC18K (Menard et al., 1993), bearing aphA-3, was ligated in the proper orientation with BspMI digested (Klenow treated) pRRS1 | Schuch and Maurelli (1999) |
| pRRS3 | The 2690 bp HindIII (Klenow treated)- EcoRI fragment of pRRS2, bearing the mxiM::aphA-3 allele, was ligated with EcoRV digested pGP704 | Schuch and Maurelli (1999) |
| pRRS4 | A 484 bp PCR generated fragment, extending from 19 bp upstream of the mxiM start codon to 26 bp downstream of the stop codon, was ligated with EcoRI-HindIII digested pBAD18 | Schuch and Maurelli (1999) |

TABLE 1-continued

Bacterial strains and plasmids.

| Strain/Plasmid | Relevant genotype/phenotype | Source/Reference |
| --- | --- | --- |
| pRRS5 | The 484 bp EcoRI-HindIII fragment of pRRS4, bearing mxiM, was ligated with EcoRI-HindIII digested pBluescript SK+ | Schuch and Maurelli (1999) |
| pRRS7 | A 2252 bp PCR generated fragment, extending from 20 bp upstream of the ipgC start codon to the stop codon of ipaB, was ligated with SmaI-HindIII digested pBAD18 | This work |
| pRRS8 | The 2276 bp NheI-HindIII fragment of pRRS7, bearing ipgC and ipaB, was ligated with SpeI-HindIII digested pBluescript SK+ | This work |
| pRRS9 | The 746 bp SmaI fragment of pRRS10, bearing gfp-mut2, was ligated in the proper orientation with SmaI digested pBAD18 | This work |
| pRRS10 | The 761 bp EcoRI-PstI fragment of pATM349, bearing gfp-mut2, was ligated with EcoRI-PstI digested pBluesript KS+ | This work |
| pRRS11 | A 370 bp PCR generated fragment, extending from 67 bp downstream of the mxiM start codon (thus deleting the signal sequence) to 10 bp downstream of the stop codon, was ligated with NdeI- BamHI digested pET19b | Schuch and Maurelli (1999) |

The following *Escherichia coli* strains were used: DH5αλpir and SM10λpir (Miller and Mekalanos, 1988), for construction of pGP704 derivatives and their delivery to *S. flexneri*; DH5α (Gibco BRL), for construction of plasmids other than pGP704 derivatives; and BL21 (DE3) (Novagen), for the overexpression and purification of mxiM.

2. Bacterial Growth and Assay Conditions

Bacteria were grown in tryptic soy broth (TSB) or L-broth (LB) with aeration at 37° C. unless otherwise stated. Strains were tested for Congo red binding on TSB agar plates (1.5% agar) containing 0.025% Congo red (Sigma). Antibiotics were used at the following concentrations: ampicillin, 100 $\mu$g ml$^{-1}$; gentamicin, 50 $\mu$g ml$^{-1}$; kanamycin, 50 $\mu$g ml$^{-1}$; and streptomycin, 200 $\mu$g ml$^{-1}$. For the induction or repression of $P_{BAD}$ transcription, growth media was supplemented with either 0.2% arabinose or 0.2% glucose, respectively. Unless otherwise stated, strains bearing pBAD18 and its derivatives were grown in the presence of arabinose.

3. Plasmid and Strain Constructions

Analysis of DNA, plasmid constructions, and the transformation of *S. flexneri* and *E. coli* were performed according to standard protocols (Sambrook et al., 1989). Polymerase chain reaction (PCR) amplifications for cloning and plasmid screening purposes were performed using Pfu (Stratagene) and HOT TUB® (Amersham) DNA polymerases, respectively, in a DNA Thermal Cycler 480 (Perkin Elmer). To confirm the fidelity of PCR reactions, all PCR generated plasmid inserts were sequenced. Templates for DNA sequencing were prepared using the ABI PRISM® Dye Terminator Cycle Sequencing Core Kit and analyzed using an ABI PRISM® 377 DNA Sequencer (Applied Biosystems, Inc.).

The wild-type mxiM locus in the virulence plasmid of *S. flexneri* 2a strain 2457T was insertionally inactivated using an aphA-3 kanamycin resistance cassette. The construction of this cassette is such that the resulting mutant mxiM1 allele (in strain B5547) was expected to have no polar effects on the expression of downstream mxi or spa loci (Menard et al., 1993).

Figure 2:
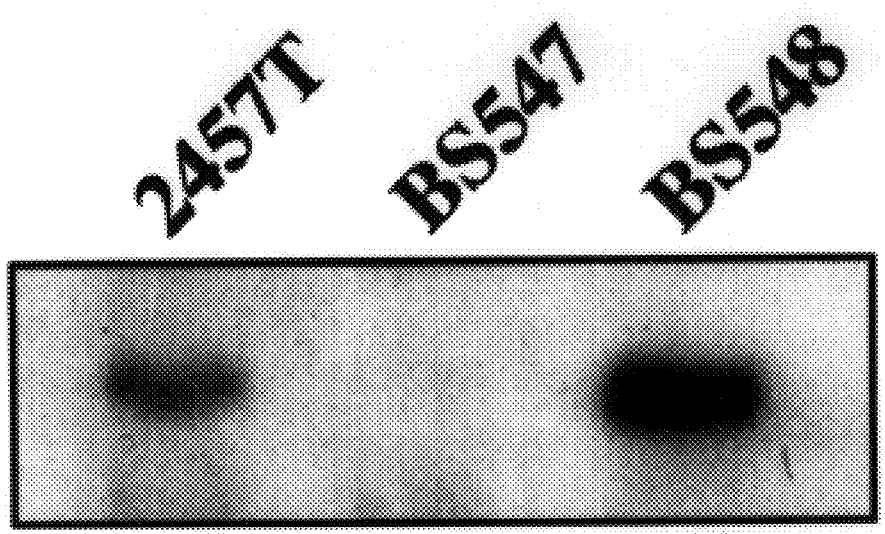

After its construction, plasmid pRRS3 was transferred to *S. flexneri* strain BS473 by conjugal mating. Transconjugants in which a double crossover recombination event replaced the virulence plasmid encoded, wild-type mxiM with the mxiM1 allele from pRRS3, were identified based on sensitivity to ampicillin and subsequent PCR analysis. The mxiM1 allele was then transferred by P1 transduction into a 2457T background creating strain BS547. The structure of the mxiM disruption in BS547 was confirmed by PCR and Southern blot analysis. The mxiM locus is predicted to encode a 142 residue protein with a calculated molecular weight of ~15 kDa. Cleavage and loss of its putative 23 residue signal sequence should yield a protein of ~13 kDa (with a pI of 8.96). A protein of the expected size for mature mxiM was detected in whole cell 2457T protein extracts by immunoblot analysis using anti-mxiM serum (FIG. 2). The corresponding protein was absent from a BS547 (mxiM1) whole cell extract, thus confirming the mxiM defect.

EXAMPLE II

Characterization of mxiM Mutants

1. Congo Red Binding

The wild type parental strain of *S. flexneri* (2457T) binds the dye Congo red when grown on nutrient agar; however, the mxiM1 mutant strain BS547 was unable to bind the dye Congo red. Congo red is a sulfonated azo dye that is bound only by colonies of virulent shigellae (Maurelli et al., 1984). Avirulent Shigella derivatives generally lose the ability to bind Congo red.

2. Virulence

The invasion assay was performed using semi-confluent L2 fibroblast monolayers. Bacterial invasion and the subsequent intracellular multiplication and firework formation was assessed in the manner described (Sandlin et al., 1996). The plaque assay was used to examine both invasion and intercellular spread through confluent L2 cell monolayers, following the procedure described by Oaks et al. (1985). The Sereny test (Sereny, 1957), which tests for virulence by the ability to induce keratoconjunctivitis in the guinea pig eye, provided an animal model for invasion and intercellular spread.

Figure 3:
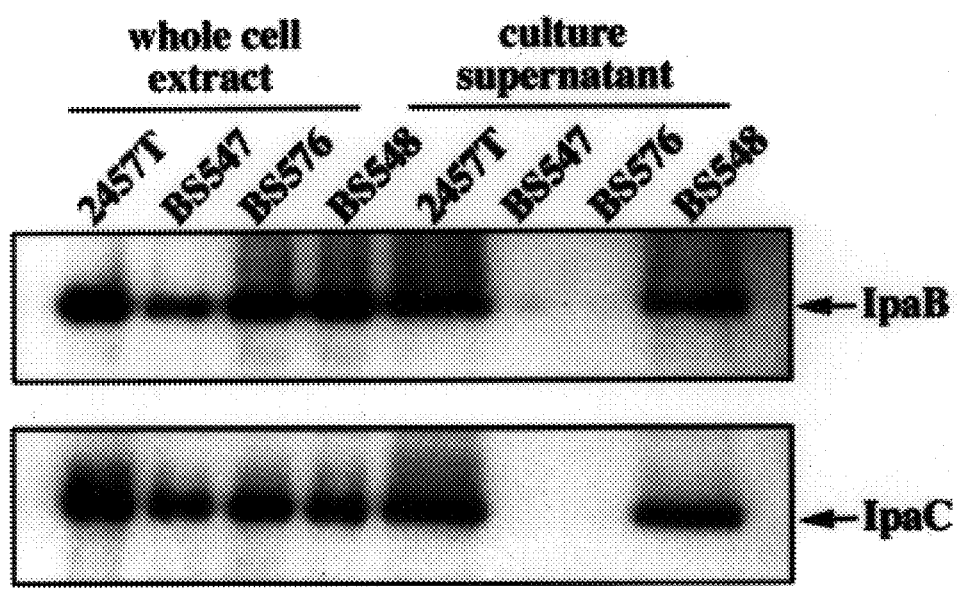

Strain BS547 was unable to invade semi-confluent L2 cell monolayers. A likely reason for this invasion defect was a block in the Ipa invasin secretory pathway. Using an anti-Ipa monoclonal antibody suspension-labeling immunoassay (the SLIM assay (Andrews and Maurelli, 1992)), we found that IpaB and IpaC secretion by strain B5547 was, in fact, blocked. Additionally, an impairment of IpaB and IpaC secretion was also detected by immunoblot analysis of BS547 supernatant proteins (FIG. 3). As has been noted in previous studies of mxi and spa mutants (Allaoui et al., 1993; Venkatesan et al., 1992), the block in secretion imparted by the mxiM1 lesion did not impair the expression of IpaB and IpaC and detection of these proteins in whole cell fractions (FIG. 3).

3. Complementation

Finally, complementation with wild-type mxiM demonstrated that the BS547 mutant phenotypes observed were strictly attributable to the absence of functional mxiM. Expression of an intact copy of mxiM from pRRS5 in strain BS575, restored Congo red binding, invasion, and IpaB and IpaC secretion to the mxiM1 mutant background. Ipa secretion defects were also complemented by expression of mxiM from the P$_{BAD}$ promoter of pRRS4 (in strain BS548) (FIG. 3). The restoration of Ipa secretion in BS548, coincided with the reappearance of mxiM in the whole cell protein fraction prepared from this strain (FIG. 2). These results demonstrated that the mxiM1 allele had no polar effects on the expression of loci with which mxiM1 is cotranscribed. The virulence defects of strain BS547, therefore, indicate that mxiM is an essential component of the Mxi-Spa type III secretion apparatus. The results are summarized in Table 2 below.

TABLE 2

Virulence phenotypes and complementation of mxiM mutants[a].

| Strain (phenotype or genotype) | Crb[b] | Invasion[c] | Secretion of[d] | |
|---|---|---|---|---|
| | | | IpaB | IpaC |
| 2457T (wild-type) | + | 85.0 | 100 | 100 |
| BS547 (mxiM1) | − | 0 | 3.1 | 5.8 |
| BS575 (mxiM1/P$_{LAC}$-mxiM$^{+}$) | + | 81.5 | 89.3 | 95.0 |
| BS588 (mxiM1/pBluescript) | − | 0 | 3.7 | 1.1 |

[a]Each value shown represents the average of at least five independent experiments.
[b]The Crb phenotype is based on a qualitative analysis of Congo red binding by bacterial colonies grown on nutrient agar.
[c]Values are expressed as a % of 300 L2 cells in a semi confluent monolayer which contained three or more internalized bacteria as determined by light microscopy.
[d]Values were determined using the SLIM assay and are expressed as a percentage of wild-type reactivity.

4. Lipidated mxiM Associates with the Outer Membrane.

Figure 4:
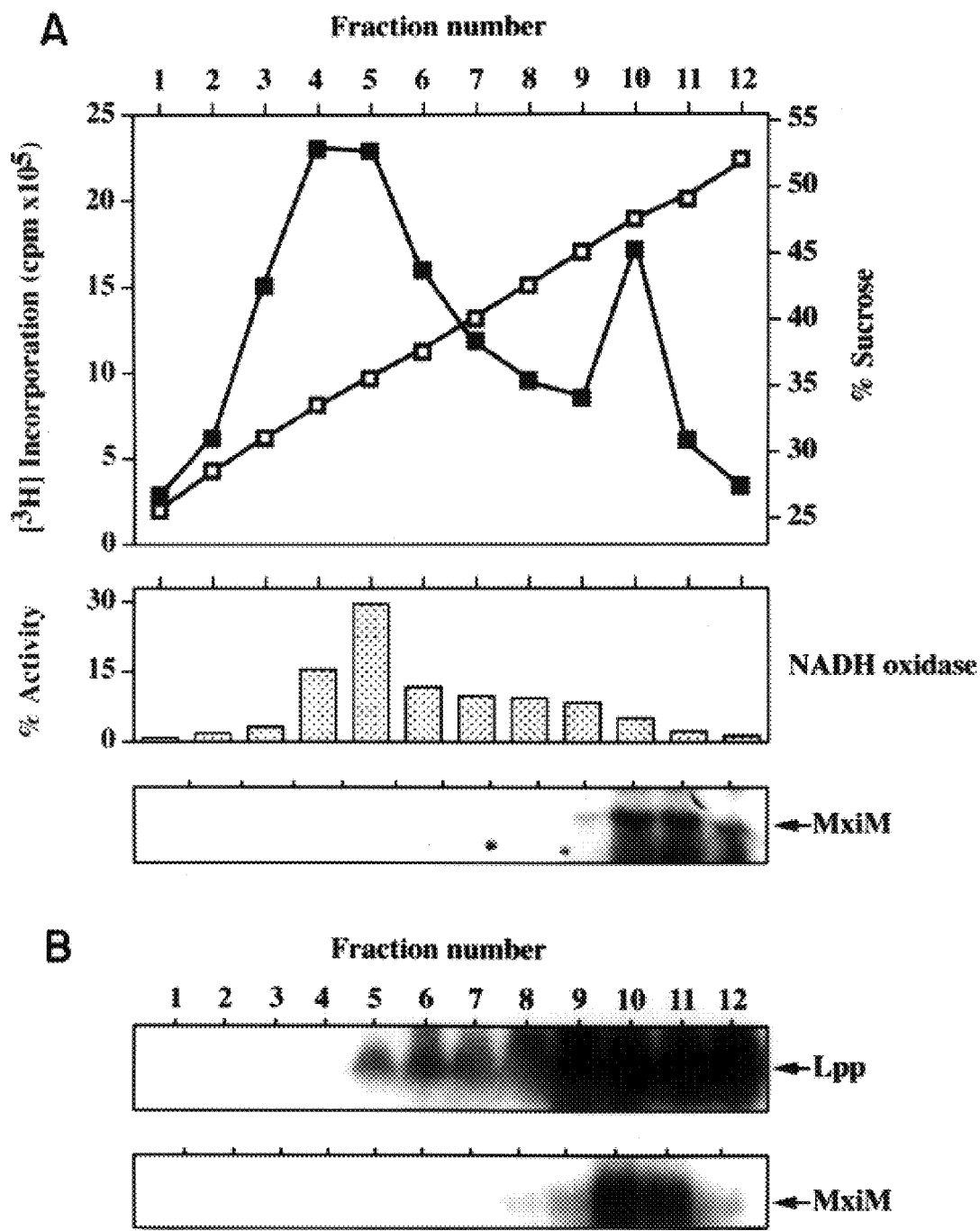

To more precisely determine the membrane position to which lipidated mxiM localizes, total cell envelope preparations isolated from both [$^3$H]palmitate-labeled and unlabeled BS548 cultures were analyzed by sucrose density gradient centrifugation. After the sedimentation of envelope components, gradient fractions of increasing sucrose density were recovered and subjected to a variety of analyses. Two distinct peaks of [$^3$H]palmitate incorporation were observed at ca. 35% (fractions 4 and 5) and 47.5% (fraction 10) w/w sucrose (FIG. 4A), likely corresponding to inner and outer membrane components, respectively. NADH oxidase activity, a control for the inner membrane (Osborne, et al., 1972), peaked in the lower density fractions (primarily in fraction 5) showing that this section of the gradient was enriched for inner membrane proteins (FIG. 4A). Immunoblot analysis of the Lpp outer membrane lipoprotein (Hankte, et al., 1973), demonstrated that the high density fractions, particularly fractions 9–12, were enriched for outer membrane proteins (FIG. 4B). A band of the appropriate size for mxiM was detected by [$^3$H]palmitate labeling and by immunoblot in the high density outer membrane protein-containing fractions (fractions 9–12) (FIG. 4A and B). This band was absent in all fractions obtained from BS548 cultures grown with glucose (the repressor of P$_{BAD}$) (data not shown). The outer membrane targeting of mxiM in BS548 was not an artifact of overexpression from the P$_{BAD}$ promoter, since the identical distribution pattern was observed in two strains in which mxiM was expressed from its native promoter (data not shown). Lipidated mxiM is therefore incorporated primarily into the outer membrane of the cell envelope.

The proper outer membrane targeting of mxiM in BS260 (an Ipa secretory mutant (Andrews et al., 1991)), indicated that its modification/processing and subsequent outer membrane association occur independent of a functional type III pathway. Consistent with this, the lipidation and localization of mxiM induced from the P$_{BAD}$ promoter of pBAD18 were unaltered in the virulence plasmid cured Shigella strain BS103 (data not shown). These results show that proper interaction between mxiM and the Sec-dependent type II secretion pathway (which likely delivers all lipoproteins across the inner membrane) and the subsequent outer membrane localization of mxiM require no accessory virulence proteins.

5. mxiM is Exposed on the Inner Face of the Outer Membrane.

A bacterial lipoprotein may exist exposed to either the periplasmic or extracellular environmnents, depending on the outer membrane face into which its N-terminal acyl chains integrate (Pugsley, 1993). To probe the topology of mxiM in the outer membrane (i.e., is it exposed at the inner or outer face), we assessed the sensitivity of mxiM pools to extracellular protease. Culture aliquots of S. flexneri 2457T were incubated with increasing amounts of proteinase K and subsequently analyzed by Western blot using antiserum recognizing either mxiM or the surface exposed protein, IcsA. Treatment of intact shigellae with proteinase K completely degraded surface exposed IcsA, but did not affect mxiM immunoblot signal intensity. Similar results were also obtained using strain BS548 (mxiM1/P$_{BAD}$-mxiM$^{+}$) (data not shown). Only after permeablization of the outer membrane by sucrose/EDTA treatment was proteolytic degradation of mxiM observed. Since denaturants were not necessary at any step to render mxiM susceptible to proteolysis, the protease resistance of mxiM is conferred by its insertion into the periplasmic face of the outer membrane.

The lipid extensions of bacterial lipoproteins are generally considered membrane anchors for otherwise hydrophillic proteins (Wu, 1996), suggesting that mxiM is probably a peripheral outer membrane protein. This is supported not only by the protease sensitivity of mxiM after outer membrane permeabilization, but by the following findings as well: (i) the mxiM fusion protein encoded by pRRS11 (which lacks an N-terminal signal sequence and is not a substrate for lipidation) was recovered only from the soluble protein fraction of cellular extracts (data not shown); and (ii) computer analyses of mxiM secondary structure (using the SOSUI and PSORT systems) predict that the protein moiety of mature mxiM is soluble in the aqueous environment of the periplasm. The bulk of mature mxiM is, therefore, likely at the interface between the outer membrane and the periplasm.

EXAMPLE III

Characterization of the P$_{BAD}$ Promoter: Expression Pattern of IcsA

We exploited observations from our in vitro virulence assays which suggested that expression of cloned, promoterless loci fused to the arabinose-inducible/glucose-repressible P$_{BAD}$ promoter of pBAD18 cannot be maintained after bacterial entry into eukaryotic cells in the absence of exogenous arabinose in the medium. For example, during growth in liquid media containing arabinose, the P$_{BAD}$ promoter in strain BS577 (ΔicsA/P$_{BAD}$-icsA$^{+}$) yielded high levels of IcsA, which properly localized at the surface of the bacterial pole (data not shown). When the induced bacteria were subsequently analyzed using the invasion and plaque assays, restoration of fireworks and plaque formation defects, respectively, were dependent on the presence of exogenous arabinose. The IcsA protein, which is polarly localized in the outer membrane, directs the polymerization of actin monomers that serve as a motor, propelling the bacterium within cellular protrusions, or fireworks, into adjacent uninfected cells (Bemardini et al., 1989; Goldberg et al., 1993). The ability to form fireworks and plaques in tissue culture monolayers are standard measures of the intercellular spread phenotype that is catalyzed, at least in part, by IcsA (Sandlin et al., 1996). The inability of $P_{BAD}$-icsA$^+$ to complement ΔicsA defects intracellularly suggested that the repression of $P_{BAD}$ was sufficiently attenuating the bacteria. By extension, it is likely that expression of any cloned gene from $P_{BAD}$ can be specifically shut off after bacterial entry into the eukaryotic cell by controlling access to arabinose.

EXAMPLE IV

The TIER (Test of Intracellular Expression Requirements) System

The TIER system is a system in which genes from pathogens are cloned into a vector system in which the gene of interest is differentially expressed.

1. gfp (Green Fluorescent Protein) Expression Patterns From $P_{BAD}$ and $P_{LAC}$ promoters To investigate the validity of our hypothesis regarding the restricted nature of $P_{BAD}$-directed gene expression during in vitro infections, we monitored expression of a $P_{BAD}$-gfp fusion in wild-type S. flexneri both before and after invasion of semi-confluent L2 cell monolayers. Two 2457T derivatives were utilized for this study, expressing gfp from either the $P_{BAD}$ promoter of pBAD18 (in BS586) or the $P_{LAC}$ promoter of pBluescript (in BS587). Because of the absence of intact lacI in pBluescript and Shigella, expression of gfp from $P_{LAC}$ in strain BS587 was expected to be constitutive within either extracellular or intracellular bacteria. Prior to invasion (0 minute infection samples), high levels of GFP-directed green or yellow fluorescence were detected emanating from extracellular populations of either BS587 or BS586 (FIG. 5A panels 1 and 3, respectively). Both the $P_{BAD}$ and $P_{LAC}$ promoters, therefore, were quite active at the outset of infection. At 120 minutes after infection, intracellular bacterial fluorescence in BS587-infected monolayers remained very strong (FIG. 5A, panel 2), indicating that the PLAC driven expression of gfp was well maintained in the intracellular environment. This expression was particularly noticeable in those bacteria displaying the intercellular spread phenotype and extending away from the infected L2 cells in protrusions. The possibility that this intracellular GFP fluorescence is attributable solely to GFP protein stability, and not to sustained intracellular $P_{LAC}$-driven gene expression, is unlikely based on results obtained from the BS586-infected monolayers. At 120 minutes after infection with strain BS586 and removal of arabinose, very little or no bacterial fluorescence was observable within the L2 intracellular environment (FIG. 5A panel 4). The arabinose-dependent expression of gfp in BS586 was, therefore, sharply diminished from pre-invasion levels subsequent to internalization. These results support a conclusion that the $P_{BAD}$-directed gene expression observed from plasmid pBAD18 in extracellular bacteria, cannot be maintained at induced levels within the L2 intracellular environment in the absence of arabinose.

2. mxiM Expression Patterns From $P_{BAD}$ and $P_{LAC}$ promoters

Based on our findings regarding $P_{BAD}$-directed gene expression, we proceeded to use the TIER system to detect specific requirements for mxiM in intercellular spread. The expression of $P_{BAD}$-mxiM1 in strain BS548 (mxiM1/$P_{BAD}$-mxiM$^+$) was clearly arabinose inducible in extracellularly located bacteria, as demonstrated by the complementation of Congo red binding, Ipa secretion, and L2 cell invasion defects resulting from the mxiM1 mutation (data not shown, FIG. 3, and Table 3, respectively). Strain BS548 was, however, unable to form plaques in confluent L2 cell monolayers in the absence of arabinose and was defective in the ability to provoke a positive Sereny reaction (an in vivo test of the intercellular spread phenotype). Therefore, the $P_{BAD}$-mxiM$^+$ fusion in BS548 was capable of supporting invasion, but not subsequent intercellular spread. When mxiM was expressed from the constitutive $P_{LAC}$ promoter of pBluescript in strain BS575 (mxiM1/$P_{LAC}$-mxiM$^+$), which should maintain high mxiM levels in the intracellular environment, intercellular spread defects were not observed and the abilities to form plaques and provoke a positive Sereny reaction were restored (Table 3). The plaque negative phenotype of BS548 was not attributable to a defect in the invasion of confluent L2 cells in the plaque assay. Two hours after infection, similar numbers of intracellular BS548, BS575, or 2457T were recoverable from infected confluent monolayers (intracellular BS547, a non-invasive control, could not be recovered) (data not shown). Taken together these results indicate a post-invasion requirement for mxiM in intercellular spread.

Firework formation observed from BS548-infected L2 cells (Table 3) indicated that internalized bacteria lysed the endocytic membrane and gained access to the eukaryotic cell cytosol. Since endosome escape is likely to be Ipa-dependent (High el al., 1992; Parsot and Sansonetti, 1996), either Ipa secretion prior to $P_{BAD}$ shutdown was sufficient to support the escape, or repression of mxiM expression was not absolute and residual levels sufficient for early Ipa secretion were achieved. Fireworks produced by internalized BS548 appeared very similar to those produced by 2457T with respect to protrusion length and the average number of protrusions per infected cell (data not shown). These similarities indicated that the process of actin-based movement was not appreciably altered by intracellular $P_{BAD}$-mxiM$^+$ shutdown. Not surprisingly then, strain BS547 (mxiM1) localized IcsA to a unipolar position on its surface, and actin-tail staining patterns (using a FITC-phalloidin stain) in BS548-infected L2 cell monolayers were indistinguishable from those patterns observed in wild-type, 2457T-infected monolayers (data not shown). These results indicate that the essential post-invasion role for mxiM in cell-to-cell spread is unrelated to the processes of endosomal lysis and firework formation, but is required for escape from protrusion membranes.

3. IpaB Expression Patterns From $P_{BAD}$ and $P_{LAC}$ promoters

Defects in Mxi-Spa secretory apparatus components which distinctly inhibit protrusion escape may exert such effects by virtue of secretion deficits. For this reason, we determined whether there was a specific Ipa requirement, similar to that observed for mxiM, in the process of intercellular dissemination. We focused on IpaB, based on its known involvement in processes involving eukaryotic membrane alterations (Menard et al., 1993; Menard et al., 1996; Zychlinsky et al., 1994), and its limited protein sequence similarity to members of a family of pore forming proteins (High et al., 1992; Zychlinsky et al., 1994). We envisioned that IpaB secretion (through Mxi-Spa) and subsequent activity may specifically mediate the process of protrusion membrane lysis.

Figure 5B:
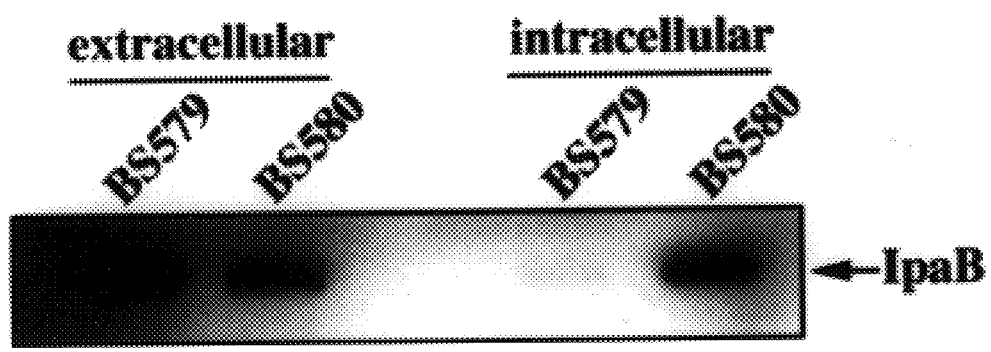

The entire ipgC and ipaB open reading frames were amplified by PCR from the virulence plasmid of 2457T and cloned into both pBAD18 and pBluescript, as described in Table 1. The ipgC locus was cloned with ipab because of a role for IpgC in the stabilization of cytoplasmic IpaB (Menard et al., 1994b). Expression of IpgC and IpaB from either pBAD18 or pBluescript, in strains BS579 (ipaB2/$P_{BAD}$-ipaB$^+$) and BS580 (ipaB2/$P_{LAC}$-ipaB$^+$), respectively, complemented defects in Congo red binding, invasion of semi-confluent L2 cell monolayers, and firework formation (data not shown, and Table 3). As with strain BS548 (mxiM1/$P_{BAD}$-mxiM$^+$), BS579 displayed no complementation in the plaque assay. When IpaB was expressed from the $P_{LAC}$ promoter in BS580, however, the ability to efficiently form plaques was restored. This difference was likely related to our findings regarding the restricted expression of genes under the control of $P_{BAD}$. To confirm this, we prepared and analyzed whole cell bacterial protein extracts, isolated from strains BS579 and BS580 either prior to L2 cell infection or 150 minutes after infection. With strain BS580, equivalent numbers of bacteria produced similar amounts of IpaB both prior to infection (extracellular pool) and after recovery from within infected L2 cell semi-confluent monolayers (intracellular pool) (FIG. 5B). With strain BS579 however, IpaB was found at very high levels prior to infection (higher than that detected in BS580), but was barely detectable in bacteria recovered from the intracellular environment 150 minutes later (FIG. 5B). These results were consistent with our findings regarding the repression of $P_{BAD}$-directed gene expression within cultured L2 cells in the absence of arabinose. The inability of intracellular BS579 to maintain high levels of IpaB expression, therefore, explains its plaque formation defect and supports a post-invasion requirement for IpaB in intercellular dissemination.

As found with strain BS548 (mxiM1/$P_{BAD}$-mxiM$^+$) above, strain BS579 (ipaB2/$P_{BAD}$-ipaB$^+$) efficiently produced projections (Table 3). Actin-tail staining patterns as well as protrusion length and frequency (the average number of projections per infected L2 cell) were nearly identical for both strains (data not shown). Additionally, both strains were completely unable to form plaques (Table 3). These findings suggest that the intracellular expression of both ipaB and mxiM are required for the same step (protrusion escape) in the process of intercellular dissemination.

TABLE 3

Distinct requirements for MxiM and IpaB in intercellular spread[a].

| Strain (phenotype or genotype)[b] | Invasion[c] | Firework Formation[d] | Plaque Formation[e] | Serény test[f] |
|---|---|---|---|---|
| 2457T (wild-type) | 83.4 | 20.1 | 2.7 | + |
| BS577 (ΔicsA/$P_{BAD}$-icsA$^+$) | 78.0 | 12.1 | 0 | nd |
| BS547 (mxiM1) | 0 | 0 | 0 | nd |
| BS548 (mxiM1/$P_{BAD}$-mxiM$^+$) | 78.5 | 18.1 | 0 | − |
| BS575 (mxiM1/$P_{LAC}$-mxiM$^+$) | 71.5 | 19.2 | 2.4 | + |
| M90T (wild-type) | 51.9 | 19.9 | 1.5 | nd |
| BS567 (ipaB2) | 0 | 0 | 0 | nd |
| BS579 (ipaB2/$P_{BAD}$-ipaB$^+$) | 47.8 | 20.0 | 0 | nd |
| BS580 (ipaB2/$P_{LAC}$-ipaB$^+$) | 52.0 | 18.8 | 1.5 | nd |

[a]All values shown represent the averages obtained from 5–10 independent experiments. In all studies involving strains BS577, BS548, and BS579, the $P_{BAD}$ promoter was induced prior to infection. Arabinose was omitted during all infections.
[b]For listed genotypes, the first designation concerns the virulence plasmid encoded allele of interest, and a second designation refers to the locus present in trans expressed from either the $P_{BAD}$ promoter of pBAD18 or the $P_{LAC}$ promoter of pBluescript SK $^+$. Strains BS577, BS547, BS548, and BS575 are derivatives of 2457T. Strains BS567, BS579, and BS580 are derivatives of M90T.

TABLE 3-continued

Distinct requirements for MxiM and IpaB in intercellular spread[a].

| Strain (phenotype or genotype)[b] | Invasion[c] | Firework Formation[d] | Plaque Formation[e] | Serény test[f] |
|---|---|---|---|---|

[c]Invasion data are expressed as percentages, determined in the manner described in Table 2.
[d]Values are expressed as the % of invaded L2 cells which displayed one or more bacteria tipped projections (fireworks).
[e]Values are expressed as a % of the total number of bacteria per infection that yielded a distinct plaque.
[f]Based on a qualitative analysis of the ability to provoke an inflammatory reaction in the corneal epithelium of guinea pigs; nd, indicates that these experiments were not done.

4. IpaC, IpaD, VirF, VirB, and Spa33 Expression Patterns From $P_{BAD}$ and $P_{LAC}$ promoters We extended our TIER analyses to the products of several known virulence genes of Shigella (including ipaC, ipaD, virF, virB, and spa33) to determine whether intercellular expression of these products after invasion of the bacterium into the host cell is required for post invasion pathogenic phenotypes. IpaC and IpaD, like IpaB, are type III-secreted effectors of Shigella virulence, required for the induction of host cell membrane alterations leading to host cell penetration (Menard et al., 1993). VirF and VirB are both transcriptional activators required for the temperature-induced expression of all ipa, mxi and spa loci (reviewed in Parsot and Sansonetti, 1996). Spa33, like mxiM, is an essential component of the Mxi-Spa secretory pathway and is required for expression of all virulence phenotypes (Schuch and Maurelli, unpublished observations).

When TIER analysis was applied to these genes, we demonstrated that intracellular repression of ipaC, ipaD, virF, virB, and spa33 completely blocked the formation of plaques while it had no effect on protrusion formation (Table 4). In contrast, when these genes were induced in the presence of arabinose, wild-type-like levels of plaque formation were restored. These results were similar to the results observed in the TIER analyses of both mxiM and ipaB and further demonstrate the utility of TIER analysis in identifying virulence genes and their products that are required for post-invasion pathogenic events.

5. Applicability of the TIER System to Analysis of Post Invasion Gene Requirements in Other Bacterial Pathogens.

Since the TIER system is designed to work with any bacterial species that supports replication of ColE1 replicon-based plasmids, the TIER system can be applied to study intracellular gene expression in a variety of other invasive bacteria. Other such bacteria include those using type III secretion systems (Salmonella spp., *Pseudomonas aeruginosa*, and pathogenic species of *E. coli*) as well as those that rely on other pathogenic strategies (Mycobacteria spp., Legionella spp., and Rickettsia).

TABLE 4

Distinct requirements for IpaC, IpaD, VirF, VirB, and Spa33 in intercellular spread[a].

| | | | Plaque formation[e] | |
|---|---|---|---|---|
| Strain phenotype or genotype[b] | Invasion[c] | Firework formation[d] | (−) arabinose | (+) arabinose |
| 2457T (wild-type) | 83.4 | 20.1 | 2.7 | NA[f] |
| ΔvirF/$P_{BAD}$-virF$^+$ | 79.0 | 19.0 | <5.6 × 10$^{-6}$ | 2.1 |
| ΔvirB/$P_{BAD}$-virB$^+$ | 84.0 | 25.0 | <5.0 × 10$^{-6}$ | 0.3 |
| Δspa33/$P_{BAD}$-spa33$^+$ | 78.5 | 17.3 | <5.0 × 10$^{-6}$ | 1.1 |

TABLE 4-continued

Distinct requirements for IpaC, IpaD,
VirF, VirB, and Spa33 in intercellular spread[a].

| Strain phenotype or genotype[b] | In-vasion[c] | Firework formation[d] | Plaque formation[e] | |
|---|---|---|---|---|
| | | | (−) arabinose | (+) arabinose |
| M90T (wild-type) | 51.9 | 19.9 | 1.5 | NA |
| ΔipaC/$P_{BAD}$-ipaC$^+$ | 89.8 | 17.5 | <6.3 × 10$^{-6}$ | 0.4 |
| ΔipaD/$P_{BAD}$-ipaD$^+$ | 81.7 | 26.2 | <4.2 × 10$^{-6}$ | 0.5 |

[a]All values shown are averages obtained from at least three independent experiments. In all studies, $P_{BAD}$ expression was induced prior to infection with 0.2% arabinose. Arabinose was omitted during the infection, except where indicated.
[b]For listed genotypes, the first designation refers to the mutant background, and the second designation refers to the locus present in trans expressed from the $P_{BAD}$ promoter of $p_{BAD18}$.
[c]Invasion data are expressed as percentages, determined in the manner described in Table 2.
[d]Values are expressed as the % of invaded L2 cells which displayed one or more bacteria tipped projections (fireworks).
[e]Values are expressed as a % of the total number of bacteria per infection that yielded a distinct plaque either in the presence or absence of arabinose.
[f]NA, not applicable.

EXAMPLE V

Expression of the mxiM Gene

In the practice of this invention, a fragment of the mxiM gene, mxiM (which may, for example, contain the his tag, such as the XbaI-BamHI fragment of pRRS11) (Table 1) is ligated to a plant promoter in an appropriate vector. The introduction of this vector in, for example, tobacco plants by appropriate methods results in the expression of mxiM, such as his-mxiM, by the tobacco plants. Once the tobacco plants are grown, they are homogenized to make a "tobacco soup" (protein extract). This soup is then used as an adsorbent for an ELISA, using standard methodology, to detect the presence of mxiM. Alternatively, this extract is run on an SDS-PAGE gel for Western blot analysis. One can use polyclonal antisera directed against the mxiM or, to detect the presence of a histidine tag, antibody directed against the his tag (available from QIAGEN) for such analysis. The amount of mxiM expressed from the plant can be quantitated using the ELISA or Western blots.

A. Construction of the Plasmid Containing the mxiM Gene.

The present example uses the vector, pKYLX 71S$^2$ (FIG. 6). This vector is obtained from David Hunt, Dept. of Crop Science, University of Kentucky, Lexington, Kentucky but those in the art will recognize that other available vectors may be used or constructed. This vector is an Agrobacterium tumefaciens binary vector containing kanamycin in vivo selectable marker gene (NPTII). A binary vector system contains two plasmids. A tumor-inducing (Ti) plasmid contains DNA (t-DNA), into which the desired coding region is inserted in a multiple cloning region. The other plasmid contains vir genes, which are virulence genes enabling the t-DNA to enter plant cells and integrate into the genome. The pKYLX 71S$^2$ vector places the desired coding sequence under the control of a doubled-enhanced cauliflower mosaic virus 35S (CaMV 35S or simply 35S) promoter. In this case, the doubled-enhanced promoter is two ribosomal promoters in tandem.

Agrobacterium vectors are useful for introducing foreign genes into a variety of plant species and particularly useful for the transformation of dicots. Numerous Agrobacterium vectors are known. See, e.g, U.S. Pat. No. 4,536,475 to Anderson, U.S. Pat. No. 4,693,977 to Schliperoort et al.; U.S. Pat. No. 4,886,937 to Sederoff et al.; T. Hall et al., EPO Application 0122791; R. Fraley et al., *Proc. Natl. Acad. Sci. USA* 84, 4803 (1983); L. Herrera-Estrella et al., *EMBO J.* 2, 987 (1983); G. Helmer et al., *Bio/Technology* 2, 520I (1984); N. Murai et al., *Science* 222, 476 (1983).

The his-mxiM gene is ligated into vector pKYLX71S$^2$, creating the DNA construct pmxiM (FIG. 6). Such vectors containing heterologous DNA can be constructed using recombinant techniques well known to those ordinarily skilled in the art. For example, DNA from pRRS11 is prepared with the use of a QIAGEN DNA extraction kit (QIAGEN, Chatsworth, Calif.). The his-mxiM gene is isolated by digestion of pRRS11 with Xbal and BamHI, separation on an agarose gel, followed by excision of the mxiM-containing band with a razor. The purified DNA is extracted from the agarose with GENECLEAN® (Bio101, LaJolla, Calif.) and ligated into pKYLX71s$^2$ digested with enzymes appropriate for cloning the mxiM containing fragment. Ligated plasmids are transformed into DH5αF'Tn5/lacI$^Q$, and transformants verified for the presence of inserted DNA by digestion with appropriate restriction enzymes. Any publicly available *Agrobacterium tumefaciens* strains may be used, but strains LBA4404, GV3850 or EHA105 (obtainable from Stanley Gelvin, Purdue University, West Lafayette, Ind.) are preferred. The pmxiM plasmid is transferred to *A. tumefaciens* using calcium-chloride ions, followed by freeze-thaw transformation, electroporation, or other methods well known to the art. See, for example, Hanahan, D., J. Mol. Biol. 166:577–80 (1983).

B. Transformation of Tobacco.

Tobacco is used very commonly as a model for plant transformation. A general assumption that had been confirmed by many empirical studies is that if a transgene is expressed in tobacco then it will be expressed in another dicot plant. Recognizing that tobacco is not an edible plant, if a recombinant mxiM is produced in tobacco, then it will be expressible in an edible plant such as canola.

Tobacco (*Nicotiana tabacum*) cultivar 'Xanthi' is transformed by Agrobacterium-mediated transformation using a standard and efficient infection protocol (Schardl et al., Gene 61: 1–11 (1987)). Briefly, tobacco leaf discs 0.5 cm in diameter are wounded and exposed to the Agrobacterium tumefaciens containing pmxiM. Plants are regenerated using an organogenic method under kanamycin selection (200 mg/L) in tissue culture.

Two hundred 0.5 cm leaf disks of tobacco are exposed to *Agrobacterium tumefaciens* harboring pmxiM. Tissue culture and plant regeneration conditions follow Schardl. et al 1987. Shoots are formed directly from wounded leaf disks under 200 mg/L kanamycin selection and 400 mg/L Timentin to kill Agrobacteria. This system is both highly efficient and not leaky (non-transgenic "escapes" are extremely rare). Three hundred and seventy-five shoots are produced from the experiment and 120 of these are arbitrarily selected for rooting on hormone-free media. All plants are morphologically normal and fertile. These results fall within the typical transformation efficiencies using this system. The high transformation frequencies and the fact that the plants are healthy indicate that mxiM is not toxic, and does not interfere with normal plant development and function.

To determine that his-mxiM is stably integrated into the plant, leaf tissue is processed according to well known methods for Southern (DNA) blot analysis (Stewart et al., Plant Physiol. 112:121–129 (1996); Stewart, C. N., Jr. and Via, L.E., Biotechniques 13: 748–751 (1993). et al.), PCR analysis (Stewart et al., Plant Physiol. 112:121–129 (1996), and Western (protein) blot analysis (Stewart et al., Plant Physiol. 112:121–129 (1996). Southern blotting is performed to verify the presence of the mxiM gene in the DNA of the leaf tissue. PCR analysis is performed to verify the presence of the mxiM gene, as well. Any appropriate primers may be used. For example, PCR amplification of putative mxiM-containing plant DNA using the appropriate primers results in the expected band when resolved on an agarose gel. Western blot analysis is performed to determine levels of expression of his-mxiM within the leaf. Once expression of his-mxiM exceeds 0.1% of total plant protein, the his-mxiM protein is isolated using a one step nickel column purification (Stolz et al., Plant Journal 6: 225–233 (1994)), although any suitable purification process may be used.

C. Preparation of Extracts

Protein extracts are recovered from putative transgenic tobacco plants as follows: Five hundred microliters of extraction buffer (20 mls 0.5 M Tris HCl pH 8.0, 4 mls 0.5 M EDTA pH 8.0, 36 mls glycerol, 20 mls β-mercaptoethanol) or 500 μl of phosphate buffer (50 mM Na-phosphate pH 7.8, 300 mM NaCl) are added to 0.2 g of leaf tissue, the mixture is homogenized on ice, and then clarified by a pulse spun in a microfuge. The supernatant is recovered, placed into a fresh eppendorf tube and stored at −70° C. Protein extracts are tested by Western blot analysis as described in Stewart et al., Plant Physiol. 112:121–129 (1996), using any of monoclonal or polyclonal anti-mxiM antibodies of the invention.

If expression of his-mxiM is hampered by, for example, high Adenine (A)/Thymine (T) content of mxiM, the gene is rebuilt using methods outlined in Adang et al. (Adang et al., 1993), incorporated herein by reference. Briefly, for the segment of mxiM contained within pmxiM, the nucleotide sequence is analyzed to determine the codon specifying each amino acid in the mxiM fragment. Capitalizing on the redundancy of the genetic code, the codons are rewritten to replace A or T with C or G without changing the amino acid specified by the codon; thus, codons of heterologous DNA, of bacterial origin, for example, are replaced with codons that are preferred for expression in a plant cell. The preferred substitutions are chosen according to the codon preference for the plant species being used. For instance, see Murray, E. E., et al., Nucleic Acids Res. 17 (2): 477–498 (1989); Dinesh-Kumar, S. P. and Miller, W. A., Plant Cell 5 (6): 679–692 (1993); Kumar, P. A. and Sharma, R. P., J. Plant Chemistry and Plant Biotechnol. 4 (2): 113–115 (1995).

EXAMPLE VI

Production of Anti-mxiM Antibody.

This example illustrates a method for preparing monoclonal antibodies that bind mxiM. Suitable immunogens that may be employed in generating such antibodies include, but are not limited to, purified mxiM polypeptide, an immunogenic fragment thereof, or fusion proteins containing mxiM.

1. Preparation of Purified mxiM Protein

The open reading frame encoding mature mxiM, lacking its 23 amino acid N-terminal signal sequence, was cloned into pET19b to create pRRS11 as described in Table 1. *E. coli* strain BL21 (DE3), bearing pRRS11, was grown at 30° C. in LB to late log phase, and induced for 4 hours in the presence of 0.5 mM IPTG. Bacteria were harvested, incubated in Tris-buffered saline (pH 7.5) containing 2 mg $ml^{-1}$ polymyxin B for 1 hour at 37° C., and centrifuged at 10,000×g for 10 min. The resulting soluble fraction, bearing the 10His-mxiM fusion protein, was filtered through 0.45 μm filters (Millipore) and purified by metal chelate affinity chromatography using 1 ml HiTrap chelating columns (Pharmacia Biotech) as described by the manufacturer. Protein was then further purified by SDS-PAGE and elution from excised gel fragments.

2. Preparation of Anti-mxiM Monoclonal Antibodies

The resulting protein preparation can be used to generate monoclonal antibodies using methods well known to those in the art. For example, purified mxiM can be used to generate monoclonal antibodies immunoreactive therewith, using conventional techniques such as those described in U.S. Pat. No. 4,411,993. Briefly, mice are immunized with mxiM immunogen emulsified in complete Freund's adjuvant, and injected in amounts ranging from 10–100 μg subcutaneously or intraperitoneally. Ten to twelve days later, the immunized animals are boosted with additional mxiM emulsified in incomplete Freund's adjuvant. Mice are periodically boosted thereafter on a weekly to bi-weekly immunization schedule. Serum samples are periodically taken by retro-orbital bleeding or tail-tip excision to test for mxiM antibodies by dot blot assay, ELISA (Enzyme-Linked Immunosorbent Assay).

Following detection of an appropriate antibody titer, positive animals are provided one last intravenous injection of mxiM in saline. Three to four days later, the animals are sacrificed, spleen cells harvested, and spleen cells are fused to a murine myeloma cell line, e.g., NS1 or preferably P3×63Ag8.653 (ATCC CRL 1580). Fusions generate hybridoma cells, which are plated in multiple microtiter plates in a HAT (hypoxanthine, aminopterin and thymidine) selective medium to inhibit proliferation of non-fused cells, myeloma hybrids, and spleen cell hybrids.

The hybridoma cells are screened by ELISA for reactivity against purified mxiM by adaptations of the techniques disclosed in Engvall et al., (Immunochem. 8:871, 1971) and in U.S. Pat. No. 4,703,004. A preferred screening technique is the antibody capture technique described in Beckmann et al., (*J. Immunol.* 144:4212, 1990). Positive hybridoma cells can be injected intraperitoneally into syngeneic BALB/c mice to produce ascites containing high concentrations of anti-mxiM monoclonal antibodies. Alternatively, hybridoma cells can be grown in vitro in flasks or roller bottles by various techniques. Monoclonal antibodies produced in mouse ascites can be purified by ammonium sulfate precipitation, followed by gel exclusion chromatography. Alternatively, affinity chromatography based upon binding of antibody to Protein A or Protein G can also be used, as can affinity chromatography based upon binding to mxiM.

Using this protocol and purified mxiM protein, monoclonal anti-mxiM (IgM) antibodies were generated.

EXAMPLE VII

Use of mxiM Antibodies to Detect mxiM Antigens

Bacterial cultures are spotted onto BAS-NC™ nitrocellulose (Schleicher & Schuell, Inc., Keene New Hampshire) through a 96-well dot blot apparatus (Schleicher & Schuell, Inc.) connected to a vacuum. The nitrocellulose membrane is air-dried and incubated for 1 hour at room temperature in phosphate-buffered saline with 0.1% TWEEN® 20 (PBS-T) (Bio-Rad Laboratories) containing 5% non-fat dry milk (Carnation Co., Los Angeles, Calif.). The membrane is washed with PBS-T and then incubated with monoclonal antibodies directed to mxiM in PBS-T for 1 hour. The membrane is washed three times with PBS-T to remove unbound antibody. The membrane is then incubated for 1 hour with a 1:500 dilution of horseradish peroxidase-conjugated goat anti-mouse immuoglobulin G antibody (Bio-Rad Laboratories) in PBS-T. After incubation, the membrane is washed five times in PBS-T, immersed in ECL™ Western blotting detection reagent (Amersham International PLC, Little Chalfont, United Kingdom) for 1 minute and then immediately exposed to X-OMAT™ film (Eastman Kodak Company, Rochester, N.Y.) for approximately 3 minutes, after which the film is developed and the presence of antigens detected.

EXAMPLE VIII

Use of mxiM DNA for DNA Based Detection Assays

The DNA of the invention or a fragment thereof can be used in assays to detect the presence of Shigella or mxiM DNA based on a labeled mxiM DNA probe using well known methods (such as those outlined in Sambrook et al., *Molecular Cloning: A Laboratory Manual*, 2nd sed., Cold Spring Harbor Laboratory, Cold Spring Harbor, N.Y. (1989)). These methods include, for example, PCR, Southern blot, colony blot and in situ hybridization, but any method may be used.

In a preferred embodiment, DNA of the sample is denatured by standard means and then eletrophoresed. The eletrophoresed DNA is transferred onto a solid support, such as a nitrocellulose filter, by methods well known in the art. To fix the DNA, the filter is air-dried and incubated for 1 hour at 80° C. in a vacuum oven. The filters are incubated in prehybridization solution (5×Denhardts, 6×SSC, 0.5% SDS, and 100 μg/mL denatured salmon sperm DNA) for 1–2 hours at 68° C. The blots are then washed twice with 2×SSC and 0.1% SDS at 68° C. for 30 minutes followed by two additional washes in 0.1×SSC and 0.5% SDS. If the probe is radiolabeled such as with $^{32}$P, the filters are removed from the final wash solution covered with SARAN WRAP®, and exposed to X-ray film.

EXAMPLE IX

Uses of maiM and ipaB Mutants of Shigella for Gene Delivery and Vaccine Production Electron microscopic analysis of tissue culture cell monolayers 5.5 hours post invasion (in the absence of arabinose) was performed to determine the nature of the plaque formation defect imposed by post-invasion repression of type III system components. We found a class of intracellular bacteria, not observed in wild-type Shigella-infected monolayers, which were lysing inside of protrusion membranes (Table 5). The association with protrusion membrane suggests that bacteria were dying during the final step in the intercellular spread process - protrusion membrane escape. These findings are supported by observations that 5–7.5 hours post-infection (in the absence of arabinose), the numbers of recoverable bacteria decrease dramatically (data not shown).

Based on these studies, the $P_{BAD}$-complemented Shigella strains described above will be useful as delivery vehicles for foreign protein and/or DNA vaccine elements. Death of the delivery vehicle (Shigella in this case) will preclude the onset of any disease symptoms after vaccine introduction. Commonly known methods in the art will be used to incorporate a gene of interest (or gene fragment) for vaccine purposes into an expression vector with a constitutively active promoter. The gene can be cloned into either the pBAD18 vector (also carrying the $P_{BAD}$-invasion gene complementing clone) or into another expression vector, compatible with pBAD18. The size and nature of the DNA will vary according to the needs of the construct. Bacteria containing the appropriate mutation in a gene essential for post invasion virulence will be transformed by any of the known methods in the art. The transformed bacteria will express the gene of interest upon introduction into the host, producing large quantities of the protein of interest and leading to antibody production. Additionally, after lysis of the bacteria in the host intracellular environment, DNA encoding the protein of interest will be released and processed by the host cell, synthesizing the encoded antigen and further promoting the immunological response against it. Determination of the appropriate dosage or effective amount, route of introduction, and the frequency of administration is well within the skills of those in the art.

The system described here allows the delivery of vaccine to the colonic mucosa, the primary site of Shigella infections. Other regions of the gastrointestinal system could be targeted through application of TIER technology to the type III systems of *Salmonella enterica* or enteropathogenic *Yersinia* spp. (which primarily infect other regions of the intestine). Transient expression of type III secretion genes in either of these backgrounds will promote initiation of an infective cycle and subsequent attenuation, thus allowing safe vaccine delivery to a particular intestinal site.

TABLE 5

Intercellular spread phenotypes determined by electron microscopy.

| Strain[a] | Cytoplasmic (not spreading)[b] | Spreading (associated with host membranes)[c] | Lysing (associated with host membranes)[d] |
|---|---|---|---|
| wild-type | 158 | 67 | 0 |
| ΔmxiM/P$_{BAD}$-mxiM$^+$ | 124 | 19 | 45 |
| ΔipaC/P$_{BAD}$-ipaC$^+$ | 76 | 24 | 52 |
| ΔipaD/P$_{BAD}$-ipaD$^+$ | 76 | 10 | 49 |

[a]5.5 hours post-infection with the indicated strains (in the absence of arabinose), samples were processed for transmission electron microscopy and analyzed.
[b]intracellular bacteria which are not in association with host cell membranes (free with the cytosol).
[c]intracellular bacteria which are in association with host cell membrane (in the process of intercellular dissemination)
[d]intracellular bacteria which are dying during the process of intercellular spread.

The person skilled in the art would understand how to use and practice the invention based on the above disclosure. Other embodiments of the invention will be apparent to those skilled in the art from consideration of the specification and practice of the invention disclosed herein. It is intended that the specification and examples be considered as exemplary only, with the true scope and spirit of the invention being indicated by the claims. The following references, as well as any references set forth above but not included here, are hereby incorporated by reference herein, and no admission is intended as to these publications constituting prior art.

References

Adam, T., Arpin, M., Prévost, M.-C., Gounon, P., and Sansonetti, P. J. (1995) Cytoskeletal rearrangements and the functional role of T-plastin during entry of *Shigella flexneri* into HeLa cells. *J Cell Biol* 129:367–381.

Adler, B., C. Sasakawa, T. Tobe, S. Makino, K. Komatsu, and M. Yoshikawa. (1989). A dual transcriptional activation system for the 230 kb plasmid genes coding for virulence-associated antigens of *Shigella flexneri. Mol. Microbiol.* 3:627–635.

Allaoui, A., Mounier, J., Prévost, M. C., Sansonetti, P. J., and Parsot, C. (1992a) icsB: a *Shigella flexneri* virulence gene necessary for the lysis of protrusions during intercellular spread. *Mol Microbiol* 6:1605–1616.

Allaoui, A., Sansonetti, P. J., and Parsot, C. (1992) MxiJ, a lipoprotein involved in secretion of Shigella Ipa invasins, is homologous to YscJ, a secretion factor of the Yersinia Yop proteins. *J Bacteriol* 174:7661–7669.

Allaoui, A., Sansonetti, P. J., and Parsot, C. (1993) MxiD: an outer membrane protein necessary for the secretion of the *Shigella flexneri* Ipa invasins. *Mol Microbiol* 7:59–68.

Andrews, G. P., Hromockyj, A. E., Coker, C., and Maurelli, A. T. (1991) Two novel virulence loci, mxiA and mxiB, in *Shigella flexneri* 2a facilitate excretion of invasion plasmid antigen. *Infect Immun* 59:1997–2005.

Andrews, G. P., and Maurelli, A. T. (1992) mxiA of *Shigella flexneri* 2a, which facilitates export of invasion plasmid antigens, encodes a homolog of the low-calcium response protein, LcrD, of *Yersinia peslis*. *Infect Immun* 60:3287–3295.

Baron, C., Thorstenson, Y. R., and Zambryski, P. C. (1997) The lipoprotein VirB7 interacts with VirB9 in the membranes of *Agrobacterium tumefaciens*. *J Bacteriol* 179:1211–1218.

Bernardini, M. L., Mounier, J., d'Hauteville, H., Coquis-Rondon, M., and Sansonetti, P. J. (1989) Identification of icsA, a plasmid locus of *Shigella flexneri* that governs bacterial intra- and intercellular spread through interaction with F-actin. *Proc Natl Acad Sci USA* 86:3867–3871.

Centers for Disease Control and Prevention. (1994). Addressing emerging infectious disease threats: A prevention strategy for the United States. U.S. Department of Health and Human Services, Public Health Service, Altanta, Ga.

Centers for Disease Control and Prevention. (1995). Summary of notifiable diseases, United States, 1995. MMWR 44:1–3.

Centers for Disease Control and Prevention. (1996). Morbidity and mortality surveillance in Rwandan refugees—Burundi and Zaire, 1994. MMWR 45:104–107.

Cormack, B. P., Valdivia, R. H., and Falkow, S. (1996) FACS-optimized mutants of the green fluorescent protein (GFP). *Gene* 173:33–38.

DuPont, H. L. (1995). Shigella species (Bacillary dysentery), p. 2033–2039. In G. L. Mandell, J. E. Bennett, and R. Dolin (eds.), Principles and practice of infectious diseases. Churchhill Livingstone Inc., New York, N.Y.

DuPont. H. L., Levine, M. M., Hornick, R. B. and Formal, S. B. (1989). Inoculum size in shigellosis and implications for expected mode of transmission. *J. Infect. Dis.* 159:1126–1128.

Formal, S. B., Dammin, G. J., LaBrec, E. H., and Schneider, H. (1958) Experimental Shigella infections: characteristics of a fatal infection produced in guinea pigs. *J Bacteriol* 75:604–610.

Fussenegger, M., Facius, D., Meier, J., and Meyer, T. F. (1996) A novel peptidoglycan-linked lipoprotein (ComI) that functions in natural transformation competance of *Neisseria gonorroeae*. *Mol Microbiol* 19:1095–1105.

Galán, J. E. and Sansonetti, P. J. (1995). Molecular and cellular bases of Salmonella and Shigella interactions with host cells. In F. D. Neidhardt, R. Curtiss III, C. A. Gross, J. I. Ingraham, E. C. Lin, K. B. Low, Jr., B. Magasnik, W. Reznikoff, M. Riley, M. Schaechter, and H. E. Umbarger (eds.), *Escherichia coli* and *Salmonella typhimurium*: Cellular and Molecular Biology, p 2757–2773. Second Edition. American Society for Microbiology, Washington, D.C.

Goldberg, M. B., Parsot, C., Barzu, O., and Sansonetti, P. J. (1993) Unipolar localization and ATPase activity of IcsA, a *Shigella flexneri* protein involved in intracellular movement. *J Bacteriol* 175:2189–2196.

Guzman, L.-M., Belin, D., Carson, M. J., and Beckwith, J. (1995) Tight regulation, modulation, and high-level expression by vectors containing the arabinose $P_{BAD}$ promoter. *J Bacteriol* 177:4121–4130.

Hankte, K., and Braun, V. (1973) Covalent binding of lipid to protein. Diglyceride and amide-linked fatty acid at the N-terminal end of the murein-lipoprotein of the *Escherichia coli* outer membrane. *Eur J Biochem* 34:284–296.

Hardie, K. R., Seydel, A., Guilvout, I., and Pugsley, A. P. (1996) The secretin-specific, chaperone-like protein of the general secretory pathway: separation of proteolytic protection and piloting finctions. *Mol Microbiol* 22:967–976.

High, N., Mounier, J., Prevost, M.-C., and Sansonetti, P. J. (1992) IpaB of *Shigella flexneri* causes entry into epithelial cells and escape from the phagocytic vacuole. *EMBO J* 11: 1991–1999.

Hueck, C. J. (1998). Type III secretion systems in bacterial pathogens of animals and plants. *Microbiol. Mol. Biol. Rev.* 62:379–433.

Institute of Medicine. (1986). The prospect for immunizing against Shigella spp., p. 329–337. In: New vaccine development: Establishing priorities. Vol. 2 Diseases of importance in developing countries. National Academy Press, Washington, D.C.

Levine, M. M., and Levine, O. S. (1994). Changes in human ecology and behavior in relation to the emergence of diarrheal diseases, including cholera. *Proc. Natl. Acad. Sci. U.S.A.* 91:2390–2394.

Maurelli, A. T., Baudry, B., d'Hauteville, H., Hale, T. L., and Sansonetti, P.J. (1985) Cloning of plasmid DNA sequences involved in invasion of HeLa cells by *Shigella flexneri*. *Infect Immun* 49:164–171.

Maurelli, A. T., Blackmon, B., and Curtiss III, R. (1984) Loss of pigmentation in *Shigella flexneri* 2a is correlated with loss of virulence and virulence-associated plasmid. *Infect Immun* 43:397–401.

Maurelli, A. T., and K. A. Lampel. 1997. Shigella species, p. 216–227. In M. P. Doyle, L. R. Beuchat, and T. J. Montville (ed.), Food Microbiology: Fundamentals and Frontiers. American Society for Microbiology Press, Washington, D.C.

Ménard, R., Dehio, C., and Sansonetti, P. J. (1996) Bacterial entry into epithelial cells: the paradigm of Shigella. *Trends Microbiol* 4:220–225.

Ménard, R., Prevost, M.-C., Gounon, P., Sansonetti, P. J., and Dehio, C. (1996) The secreted Ipa complex of *Shigella flexneri* promotes entry into mammalian cells. *Proc Natl Acad Sci USA* 93:1254–1258.

Ménard, R., Sansonetti, P. J., and Parsot, C. (1993) Nonpolar mutagenesis of the ipa genes defines IpaB, IpaC, and IpaD as effectors of *Shigella flexneri* entry into epithelial cells. *J Bacteriol* 175:5899–5906.

Ménard, R., Sansonefti, P. J., Parsot, C., and Vasselon, T. (1994b) Extracellular association and cytoplasmic partitioning of the IpaB and IpaC invasins of *S. flexneri*. *Cell* 79:515–525.

Menard, R., Sansonetti, P. J., Parsot, C. and Vasselon, T. (1994). The IpaB and IpaC invasins of *Shigella flexneri* associate in the extracellular medium and are partitioned in the cytoplasm by a specific chaperone. *Cell* 76:829–839.

Miller, V. L., and Mekalanos, J. J. (1988) A novel suicide vector and its use in construction of insertion mutations;

osmoregulation of outer membrane proteins and virulence determinants in *Vibrio cholerae* requires ToxR. *J Bacteriol* 173:4994–5009.

Mohle-Boetani, J. C., Stapleton, M., Finger, R., Bean, N. H., Poundstone, J., Blake, P. A. and Griffin, P. M. (1995). Comrnunitywide shigellosis: control of an outbreak and risk factors in child day-care centers. *Am. J. Public Health* 85:812–816.

Oaks, E. V., Hale, T. L., and Formal, S. B. (1986). Serum immune response to Shigella protein antigens in rhesus monkeys and humans infected with Shigella spp. *Infect. Immun.* 53:57–63.

Oaks, E. V., Wingfield, M. E., and Formal, S. B. (1985) Plaque formation by virulent *Shigella flexneri*. *Infect Immun* 48:124–129.

Ochman, H., Whittam, T. S., Caugant, D. A., and Selander, R. K. (1983). Enzyme polymorphism and genetic population structure in *Escherichia coli* and Shigella. *J. Gen. Microbiol.* 129:2715–2726.

Osborn, M. J., Gander, J. E., Parisi, E., and Carson, J. (1972) Mechanism of assembly of the outer membrane of *Salmonella typhimurium*. *J Biol Chem* 247:3962–3972.

Paquet, C., P. Leborgne, A. Sasse, and F. Varaine. (1995). Une epidemie de dysenteriae á *Shigella dysenteriae* type 1 dans un camp de refugies au Rwanda (An outbreak of *Shigella dysenteriae* type 1 dysentery in a refugee camp in Rwanda). *Santé*5:181–184.

Parsot, C., Menard, R., Gounon, P., and Sansonetti, P. J. (1995) Enhanced secretion through the *Shigella flexneri* Mxi-Spa translocon leads to assembly of extracellular proteins into macromolecular structures. *Mol Microbiol* 16:291–300.

Parsot, C., and Sansonetti, P. J. (1996) Invasion and pathogenesis of Shigella infections. In *Bacterial invasiveness*. Miller, V. L. (ed.). N.Y.:Springer-Verlag, pp. 25–42.

Pugsley, A. P. (1993) The complete general secretory pathway in Gram-negative bacteria. *Microbiol Rev* 57:50–108.

Ramer, S. W., Bieber, D., and Schoolnik, G. (1996) BfpB, an outer membrane lipoprotein required for the biogenesis of bundle-forming pili in enteropathogenic *Escherichia coli*. *J Bacteriol* 178:6555–6563.

Rugh, C. L., Wilde, H. D., Stack, N. M., Thompson, D. M., Summers, A. O., and Meagher, R. B. (1996). Mercuric ion reduction and resistance in transgenic *Arabidopsis thaliana* plants expressing a modified bacterial merA gene. *Proc. Natl. Acad. Sci. USA* 93: 3182–3187.

Sakai, T., Sasakawa, C., Makino, S., Yoshikawa, M. (1986). DNA sequence and product analysis of the virF locus responsible for congo red binding and cell invasion in *Shigella flexneri* 2a. *Infect. Immun.* 54:395–402.

Sambrook, J., Fritsch, E. F., and Maniatis, T. (1989) *Molecular cloning: A Laboratory Manual*. Cold Spring Harbor, N.Y.: Cold Spring Harbor Laboratory Press.

Sandlin, R. C., Goldberg, M. B., and Maurelli, A. T. (1996) Effect of O side-chain length and composition on the virulence of *Shigella flexneri* 2a. *Mol Microbiol* 22:63–73.

Sansonetti, P. J., Hale, T. L., and Oaks, E. V. (1985). Genetics of virulence in enteroinvasive *Escherichia coli*, p. 74–77. In D. Schlessinger (ed.), Microbiology—1985. American Society for Microbiology, Washington, D.C.

Sansonetti, P. J., Kopecko, D. J., and Formal, S. B. (1982) Involvement of a plasmid in the invasive ability of *Shigella flexneri*. *Infect Immun* 35:852–860.

Sansonetti, P. J., Ryter, A., Clerc, P., Maurelli, A. T., and Mounier, J. (1986) Multiplication of *Shigella flexneri* within HeLa cells: lysis of the phagocytic vacuole and plasmid-mediated contact hemolysis. *Infect Immun* 51:461–469.

Sasakawa, C., Komatsu, K., Tobe, T., Suzuki, T., and Yoshikawa, M. (1993) Eight genes in region 5 that form an operon are essential for invasion of epithelial cells by *Shigella flexneri* 2a. *Infect Immun* 175:2334–2346.

Schuch, R., and A. T. Maurelli. (1999). The Mxi-Spa type III secretory pathway of *Shigella flexneri* requires an outer membrane lipoprotein, mxiM, for invasin translocation. *Infect. Immun.* 67:1982–1991.

Serény, B. (1957) Experimental keratoconjunctivitis shigelosa. *Acta Microbiol Acad Sci Hung* 4:367–376.

Sizemore, D., Branstrom, A., and Sadoff, J. (1995) Attenuated Shigella as a DNA delivery vehicle for DNA-mediated immunization. *Science* 270:299–302.

Sizemore, D., Branstrom, A., and Sadoff, J. (1997) Attenuated bacteria as a DNA delivery vehicle for DNA-mediated immunization. *Vaccine* 15(8):804–807.

Tran Van Nhieu, G., Ben-Zéev, A., and Sansonetti, P. J. (1997) Modulation of bacterial entry into epithelial cells by association between vinculin and the Shigella IpaA invasin. *EMBO J* 16:2717–2729.

Venkatesan, M. M., Buysse, J. M., and Oaks, E. V. (1992) Surface presentation of *Shigella flexneri* invasion plasmid antigens requires products of the spa locus. *J Bacteriol* 174:1990–2001.

Wu, H. C. (1996). Biosynthesis of lipoproteins, p. 1005–1014. In F.C. Niedhardt, R. Curtiss III, J. L. Ingraham, E. C. C. Lin, K. B. Low, B. Magasanik, M. Riley, W. S. Reznikoff, M. Schaechter, and H. E. Umbarger (ed.), *Escherichia coli* and Salmonella: cellular and molecular biology, 2nd ed. American Society of Microbiology Press, Washington, D.C.

Zychlinsky, A., Kenny, B., Menard, R., Prevost, M.-C., Holland, I. B., and Sansonetti, P. J. (1994) IpaB mediates macrophage apoptosis induced by *Shigella flexneri*. *Mol Microbiol* 11:619–627.

We claim:

1. A method of detecting Shigella or Shigella mxiM (Membrane eXpression of Invasion plasmid antigen M) DNA in a sample comprising:

(a) introducing a labeled Shigella mxiM DNA probe to said sample and (b) detecting any binding between the Shigella mxiM DNA probe and Shigella mxiM DNA in the sample, wherein binding indicates the presence of Shigella or Shigella mxiM DNA.

2. The method in accordance to claim 1, wherein said binding is assessed using a method selected from polymerase chain reaction, Southern blot, and in situ hybridization.

3. The method of claim 1, wherein said sample contains a gene delivery vector comprising Shigella mxiM DNA.

* * * * *

UNITED STATES PATENT AND TRADEMARK OFFICE
CERTIFICATE OF CORRECTION

PATENT NO.   : 6,342,352 B1                                           Page 1 of 1
DATED        : January 29, 2002
INVENTOR(S)  : Raymond Schuch, Robin C. Sandlin and Anthony T. Maurelli It is certified that error appears in the above-identified patent and that said Letters Patent is hereby corrected as shown below:

<u>Title page,</u>
Item [54], Title, please delete "OF" before "DETECTING" and insert therefor
-- FOR --.

Item [57], ABSTRACT,
Line 3, please delete "Shigella" and insert therefor -- Shigellae --.

<u>Column 35,</u>
Line 54, please delete "sample comprising" and insert therefor -- sample suspected of containing Shigella or Shigella mxiM DNA comprising --.
Line 59, please delete "and Shigella" and insert therefor -- and the Shigella --.

<u>Column 36,</u>
Line 51, please delete "wherein binding" and insert therefor -- wherein said binding --.

Signed and Sealed this

Twentieth Day of August, 2002

*Attest:*

JAMES E. ROGAN
*Attesting Officer*     *Director of the United States Patent and Trademark Office*